US011047860B2

(12) United States Patent
Liebler et al.

(10) Patent No.: US 11,047,860 B2
(45) Date of Patent: Jun. 29, 2021

(54) PROTEIN QUANTITATION IN MULTICELLULAR TISSUE SPECIMENS

(71) Applicant: Vanderbilt University, Nashville, TN (US)

(72) Inventors: Daniel C. Liebler, Brentwood, TN (US); Lisa J. Zimmerman, Franklin, TN (US); Robbert J. C. Slebos, Baltimore, MD (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 15/773,719

(22) PCT Filed: Apr. 20, 2016

(86) PCT No.: PCT/US2016/028426
§ 371 (c)(1),
(2) Date: May 4, 2018

(87) PCT Pub. No.: WO2017/078787
PCT Pub. Date: May 11, 2017

(65) Prior Publication Data
US 2019/0154699 A1 May 23, 2019

Related U.S. Application Data

(60) Provisional application No. 62/251,604, filed on Nov. 5, 2015.

(51) Int. Cl.
*G01N 31/00* (2006.01)
*G01N 33/53* (2006.01)
*G01N 33/68* (2006.01)

(52) U.S. Cl.
CPC ................ *G01N 33/6848* (2013.01)

(58) Field of Classification Search
None
See application file for complete search history.

(56) References Cited

U.S. PATENT DOCUMENTS

| | | | |
|---|---|---|---|
| 6,174,293 B1 | 1/2001 | Buck et al. | |
| 2007/0019854 A1 | 1/2007 | Gholap et al. | |
| 2008/0226554 A1* | 9/2008 | Colgan ............ | G01N 33/57484 424/9.1 |
| 2008/0312260 A1 | 12/2008 | Haley et al. | |
| 2011/0306514 A1 | 12/2011 | Hewitt et al. | |
| 2014/0234854 A1* | 8/2014 | Blume ............ | G01N 33/57419 435/7.1 |
| 2016/0313343 A1 | 10/2016 | Krizman et al. | |

FOREIGN PATENT DOCUMENTS

| | | | |
|---|---|---|---|
| EP | 02309262 | * 4/2011 | ............ G01N 33/50 |
| EP | 2309262 A1 | 4/2011 | |
| JP | 2010533836 A | 10/2010 | |
| JP | 2012515334 A | 7/2012 | |
| WO | WO2013165598 | 11/2013 | |

OTHER PUBLICATIONS

Abbatiello et al., "Design, implementation and multisite evaluation of a system suitability protocol for the quantitative assessment of instrument performance in liquid chromatography-multiple reaction monitoring-MS (LC-MRM-MS)," Mol Cell Proteomics, 2013; 12: 2623-2639.
Abbatiello et al., "Large-Scale Interlaboratory Study to Develop, Analytically Validate and Apply Highly Multiplexed, Quantitative Peptide Assays to Measure Cancer-Relevant Proteins in Plasma," Mol Cell Proteomics 2015; 14: 2357-2374.
Addona et al., "Multi-site assessment of the precision and reproducibility of multiple reaction monitoring-based measurements of proteins in plasma," Nat Biotechnol. Jul. 2009;27(7):633-41.
Anderson, "Tim-3: an emerging target in the cancer immunotherapy landscape," Cancer Immunol Res., 2014; 2: 393-398.
Bassani-Sternberg et al., "Mass spectrometry-based antigen discovery for cancer immunotherapy," Curr Opin Immunol., 2016; 41:9-17. doi: 10.1016/j.coi.2016.04.005.
Borghaei et al., "Nivolumab versus Docetaxel in Advanced Nonsquamous Non-Small-Cell Lung Cancer," N Engl J Med., 2015; 373: 1627-1639.
Brahmer et al., "Nivolumab versus Docetaxel in Advanced Squamous-Cell Non-Small-Cell Lung Cancer," N Engl J Med., 2015; 373: 123-135.
Chen et al., "Quantification of β-Catenin Signaling Components in Colon Cancer Cell Lines, Tissue Sections, and Microdissected Tumor Cells using Reaction Monitoring Mass Spectrometry," J. Proteome Res., 2010; 9:4215-4227.
Chen et al., (2009) Glycoproteomics analysis of human liver tissue by combination of multiple enzyme digestion and hydrazide chemistry. J Proteome Res 8, 651-661.
Chen et al., (2016) Analysis of Immune Signatures in Longitudinal Tumor Samples Yields Insight into Biomarkers of Response and Mechanisms of Resistance to Immune Checkpoint Blockade. Cancer Discov 6, 827-837.
Dahan et al., (2016) Therapeutic Activity of Agonistic, Human Anti-CD40 Monoclonal Antibodies Requires Selective FcgammaR Engagement. Cancer Cell 29, 820-831.
Danilova et al., (2016) Association of PD-1/PD-L axis expression with cytolytic activity, mutational load, and prognosis in melanoma and other solid tumors. Proc Natl Acad Sci U S A 113, E7769-E7777.
Daud et al., (2016) Programmed Death-Ligand 1 Expression and Response to the Anti-Programmed Death 1 Antibody Pembrolizumab in Melanoma. J Clin Oncol 34, 4102-4109.
Dezutter-Dambuyant et al., (2016) A novel regulation of PD-1 ligands on mesenchymal stromal cells through MMP-mediated proteolytic cleavage. Oncoimmunology 5, e1091146, 24 pages.

(Continued)

Primary Examiner — Lisa V Cook
(74) Attorney, Agent, or Firm — Michael Best & Friedrich LLP

(57) ABSTRACT

Provided are methods for measuring the amount of a target protein in a heterogeneous multicellular biospecimen having two or more cell types.

21 Claims, 8 Drawing Sheets
Specification includes a Sequence Listing.

(56) References Cited

OTHER PUBLICATIONS

Drabovich et al., (2012) Quantitative analysis of energy metabolic pathways in MCF-7 breast cancer cells by selected reaction monitoring assay. Mol Cell Proteomics 11, 422-434.
Federspiel et al., (2016) Assembly Dynamics and Stoichiometry of the Apoptosis Signal-regulating Kinase (ASK) Signalosome in Response to Electrophile Stress. Mol Cell Proteomics 15, 1947-1961.
Ferris et al., (2016) Nivolumab for Recurrent Squamous-Cell Carcinoma of the Head and Neck. N Engl J Med, 12 pages.
Gallien et al., "Targeted proteomic quantification on quadrupole-orbitrap mass spectrometer," Mol Cell Proteomics. Dec. 2012;11(12):1709-23.
Gold et al., "Aptamer-based multiplexed proteomic technology for biomarker discovery," PLoS One. Dec. 7, 2010;5(12):e1500, 17 pages.
Hutton et al., (2016) Oncogenic KRAS and BRAF Drive Metabolic Reprogramming in Colorectal Cancer. Mol Cell Proteomics 15, 2924-2938.
International Search Report and Written Opinion for Application No. PCT/US2016/028426, dated Jul. 18, 2016, 9 pages.
Joyce et al., (2015) T cell exclusion, immune privilege, and the tumor microenvironment. Science 348, 74-80.
Keir et al., PD-1 and its ligands in tolerance and immunity, Annu Rev Immunol, 2008; 26, 677-704.
Kikuchi et al., "In-depth proteomic analysis of nonsmall cell lung cancer to discover molecular targets and candidate biomarkers," Mol Cell Proteomics. Oct. 2012;11(10):916-32.
Kim et al., (2016) Quantitative Profiling of Protein Tyrosine Kinases in Human Cancer Cell Lines by Multiplexed Parallel Reaction Monitoring Assays. Mol Cell Proteomics 15, 682-691.
Larkin et al., "Combined Nivolumab and Ipilimumab or Monotherapy in Untreated Melanoma," N Engl J Med., 2015; 373, 23-34.
Latchman et al., (2001) PD-L2 is a second ligand for PD-1 and inhibits T cell activation. Nat Immunol 2, 261-268.
Le Mercier et al., (2014) VISTA Regulates the Development of Protective Antitumor Immunity. Cancer Res 74, 1933-1944.
Lee et al., (2014) Abundance-ratio-based semiquantitative analysis of site-specific N-linked glycopeptides present in the plasma of hepatocellular carcinoma patients. J Proteome Res 13, 2328-2338.
Li et al., (2016) Glycosylation and stabilization of programmed death ligand-1 suppresses T-cell activity. Nat Commun 7, 12632, 11 pages.
Lines et al., (2014) VISTA is a novel broad-spectrum negative checkpoint regulator for cancer immunotherapy. Cancer Immunol Res 2, 510-517.
Lizotte et al., (2016) Multiparametric profiling of non-small-cell lung cancers reveals distinct immunophenotypes. JCI Insight 1, e89014, 18 pages.
Maclean et al., "Skyline: an open source document editor for creating and analyzing targeted proteomics experiments," Bioinformatics. Apr. 1, 2010;26(7):966-8.
Mahoney et al., (2015) Combination cancer immunotherapy and new immunomodulatory targets. Nat Rev Drug Discov 14, 561-584.
Mani et al., "Statistical characterization of multiple-reaction monitoring mass spectrometry (MRM-MS) assays for quantitative proteomics," BMC Bioinformatics. 2012;13 Suppl 16:S9, 18 pages.
Motzer et al., "Nivolumab versus Everolimus in Advanced Renal-Cell Carcinoma," N Engl J Med., 2015; 373, 1803-1813.
Nguyen et al., (2015) Clinical blockade of PD1 and LAG3—potential mechanisms of action. Nat Rev Immunol 15, 45-56.
Pardoll, "The blockade of immune checkpoints in cancer immunotherapy," Nat Rev Cancer, 2012; 12, 252-264.
Peterson et al., (2012) Parallel reaction monitoring for high resolution and high mass accuracy quantitative, targeted proteomics. Mol Cell Proteomics 11, 1475-1488.
Platten et al., (2014) Cancer Immunotherapy by Targeting IDO1/TDO and Their Downstream Effectors. Front Immunol 5, 673, 7 pages.
Polyakova et al., "Proteogenomics meets cancer immunology: mass spectrometric discovery and analysis of neoantigens," Expert Rev. Proteomics,2015; 12(5): 533-541.
Rauniyar, "Parallel Reaction Monitoring: A Targeted Experiment Performed Using High Resolution and High Mass Accuracy Mass Spectrometry," Int J Mol Sci. Dec. 2015; 16(12): 28566-28581.
Reck et al., (2016) Pembrolizumab versus Chemotherapy for PD-L1-Positive Non-Small-Cell Lung Cancer. N Engl J Med. 1823-1833.
Ribas et al., "Pembrolizumab versus investigator-choice chemotherapy for ipilimumab-refractory melanoma (KEYNOTE-002): a randomised, controlled, phase 2 trial," Lancet Oncol, 2015; 16, 908-918.
Rizvi et al., (2015) Cancer immunology. Mutational landscape determines sensitivity to PD-1 blockade in non-small cell lung cancer. Science 348, 124-128.
Robert et al., "Pembrolizumab versus Ipilimumab in Advanced Melanoma," N Engl J Med., 2015; 372, 2521-2532.
Rosenberg et al., (2016) Atezolizumab in patients with locally advanced and metastatic urothelial carcinoma who have progressed following treatment with platinum-based chemotherapy: a single-arm, multicentre, phase 2 trial. Lancet 387, 1909-1920.
Rosner et al., (1982) Separation of glycopeptides by high performance liquid chromatography. J Cell Biochem 18, 37-47.
Schumacher et al., (2015) Neoantigens in cancer immunotherapy. Science 348, 69-74.
Sharma et al., (2015) Immune checkpoint targeting in cancer therapy: toward combination strategies with curative potential. Cell 161, 205-214.
Sharma et al., (2016) Nivolumab monotherapy in recurrent metastatic urothelial carcinoma (CheckMate 032): a multicentre, open-label, two-stage, multi-arm, phase 1/2 trial. Lancet Oncol 17, 1590-1598.
Shi et al., (2012) Antibody-free, targeted mass-spectrometric approach for quantification of proteins at low picogram per milliliter levels in human plasma/serum. Proc Natl Acad Sci U S A 109, 15395-15400.
Sholl et al., (2016) Programmed Death Ligand-1 Immunohistochemistry—A New Challenge for Pathologists: A Perspective From Members of the Pulmonary Pathology Society. Arch Pathol Lab Med 140, 341-344.
Sjöström et al., "A Combined Shotgun and Targeted Mass Spectrometry Strategy for Breast Cancer Biomarker Discovery," J Proteome Res. Jul. 2, 2015;14(7):2807-18. doi: 10.1021/acs.jproteome.5b00315. Epub Jun. 5, 2015.
Sprung et al., (2012) Precision of multiple reaction monitoring mass spectrometry analysis of formalin-fixed, paraffin-embedded tissue. J Proteome Res 11, 3498-3505.
Sunshine et al., (2015) PD-1/PD-L1 inhibitors. Curr Opin Pharmacol 23, 32-38.
Topalian et al., "Mechanism-driven biomarkers to guide immune checkpoint blockade in cancer therapy," Nature Reviews Cancer 16, 275-287 (2016).
Tumeh et al., "PD-1 blockade induces responses by inhibiting adaptive immune resistance," Nature. Nov. 27, 2014;515(7528):568-71.
Yoshihara et al., "Inferring tumour purity and stromal and immune cell admixture from expression data," Nat Commun. 2013; 4:2612, 11 pages.
Youngnak et al., (2003) Differential binding properties of B7-H1 and B7-DC to programmed death-1. Biochem Biophys Res Commun 307, 672-677.
Zak et al., (2015) Structure of the Complex of Human Programmed Death 1, PD-1, and Its Ligand PD-L1. Structure 23, 2341-2348.
Zhang et al., "Proteogenomic characterization of human colon and rectal cancer," Nature. Sep. 18, 2014;513(7518):382-7.
Zhang et al., (2011) Methods for peptide and protein quantitation by liquid chromatography-multiple reaction monitoring mass spectrometry. Mol Cell Proteomics 10, M110 006593.
Zou et al., (2016) PD-L1 (B7-H1) and PD-1 pathway blockade for cancer therapy: Mechanisms, response biomarkers, and combinations. Sci Transl Med 8, 328rv324.
European Patent Office Search Report for Application No. 16862613.3 dated Apr. 1, 2019, 7 pages.

(56) References Cited

OTHER PUBLICATIONS

European Patent Office Examination Report for Application No. 16862613.3 dated Mar. 25, 2020 (4 pages).
Translation of Japanese Patent Office Action for Application No. 2018-542117 dated Apr. 7, 2020 (2 pages).

* cited by examiner

Fig. 7

| Protein Name | Peptide Sequence | Specimen content (fmol/microgram tissue protein) | | | | | | | |
|---|---|---|---|---|---|---|---|---|---|
| | | 1 | 2 | 3 | 4 | 5 | 6 | 7 | 8 |
| ERBB1 | IPLENLQIR | 2.0 | 2.1 | 0.7 | 0.4 | 1.1 | 2.5 | 0.2 | 0.5 |
| ACTB | GYSFTTTAER | 2264.4 | 2980.3 | 3825.9 | 1235.3 | 2279.7 | 2547.4 | 1908.7 | 1657.7 |
| RALY | GYAFVQYSNER | 2.9 | 2.6 | 3.9 | 1.3 | 1.8 | 2.8 | 2.3 | 4.4 |
| Carcinoma component-specific factor | | 0.00129 | 0.00088 | 0.00101 | 0.00101 | 0.00080 | 0.00108 | 0.00122 | 0.00265 |
| ERBB1 target value | | 1518.7 | 2405.1 | 728.7 | 418.6 | 1437.9 | 2268.4 | 131.3 | 201.5 |

PROTEIN QUANTITATION IN MULTICELLULAR TISSUE SPECIMENS

RELATED APPLICATION INFORMATION

This application claims priority from U.S. Patent Application No. 62/251,604, filed on Nov. 5, 2015, which is hereby incorporated by reference in its entirety.

STATEMENT REGARDING FEDERALLY SPONSORED RESEARCH

This invention was made with U.S. Government support under grant number U24CA159988 awarded by the National Institutes of Health. The U.S. Government has certain rights in this invention.

TECHNICAL FIELD

This disclosure relates to the analysis of proteins in heterogeneous biospecimens.

BACKGROUND

Various disorders and diseases, including cancers, arise from alterations in the sequence, structure, or expression of genes that control cell function, growth, and differentiation. These alterations lead to distinct sets of changes in RNAs, proteins and other biomolecules, which drive clinically important characteristics, such as the propensity of a cancer to invade nearby tissues, metastasize to other organs and respond to therapies. Of these molecular features, proteins are often the targets of drugs for disease treatment. In some cases, drugs are targeted specifically to protein sequence variants encoded by genes that are mutated or dysregulated in cancers or other diseases. Diagnostic tests may also measure other proteins that are not themselves targets, but which affect the functions of drug targets and thereby influence the response of a disease to treatment.

The predominant method to analyze proteins in tissue specimens is immunohistochemistry (IHC), in which a protein of interest is detected in a thin tissue section by reaction with an antibody, followed by a staining procedure that enables visualization of the antibody-detected proteins by microscopy. Because a skilled pathologist can distinguish different cell types and stroma in the section, the association of the staining with the cells of interest or surrounding stroma can be verified, thereby providing evidence of association of the detected protein with the cells of interest, such as cancer cells. This is particularly important because tissue specimens are usually heterogeneous and vary widely in the proportional composition of various cell types, such as cancer cells, stroma, normal epithelial cells, smooth muscle, fat, immune cells, and other cell types.

Despite widespread use, IHC has significant limitations. IHC analysis requires an antibody that specifically and selectively binds to the protein of interest in a section. For many proteins, antibodies with the necessary performance characteristics for IHC cannot be obtained. In the most widely used diagnostic implementation, IHC detects one protein in each of one or more thin sections of a tissue specimen tested, and the measurement of multiple protein features is practically limited. Moreover, many IHC tests fail to yield interpretable results because of problems with the antibody recognition of the target protein or with the staining chemistry and because of variability in quality of the tissue sections due to sample handling, processing, and storage.

SUMMARY

The present disclosure provides a method for measuring the amount of a target protein in a heterogeneous biospecimen having two or more cell types. The method may comprise extracting proteins from a heterogeneous biospecimen; cleaving the proteins to form peptides; and analyzing the peptides by mass spectrometry to measure an amount of a proteotypic peptide of a benchmark protein, an amount of a proteotypic peptide of a component-specific protein, and an amount of a proteotypic peptide of a target protein. The method may further comprise quantifying an amount of the benchmark protein, an amount of the component-specific protein, and an amount of the target protein in the biospecimen based on the amounts of the corresponding proteotypic peptides; normalizing the amount of the component-specific protein to the amount of the benchmark protein to identify a component factor of a component cell type that expresses the component-specific protein; and normalizing the amount of the target protein to the component factor of the component cell type to identify a component factor adjusted amount representing a target value of the target protein in the heterogeneous biospecimen. The component factor may be identified as the ratio of the measured amount of the benchmark protein to the measured amount of the component-specific protein.

Also provided are methods for quantifying a target protein in a heterogeneous biospecimen comprising obtaining proteins extracted from a heterogeneous biospecimen; quantifying an amount of a benchmark protein, an amount of a component-specific protein, and an amount of a target protein extracted from the biospecimen; normalizing the amount of the component-specific protein to the amount of the benchmark protein to identify a component factor of a component cell type that expresses the component-specific protein; and normalizing the amount of the target protein to the component factor of the component cell type to identify a component factor adjusted amount of the target protein representing a target value of the target protein in the heterogeneous biospecimen.

BRIEF DESCRIPTION OF THE DRAWINGS

FIG. 7 provides the measured content of target protein (ERBB1), component-specific protein (RALY), and benchmark protein (ACTB) in eight biospecimens containing colon carcinoma cells by detecting the indicated proteotypic peptides for each protein. The component-specific factors and ERBB1 target values were prepared for each sample.

DETAILED DESCRIPTION

Figure 1:
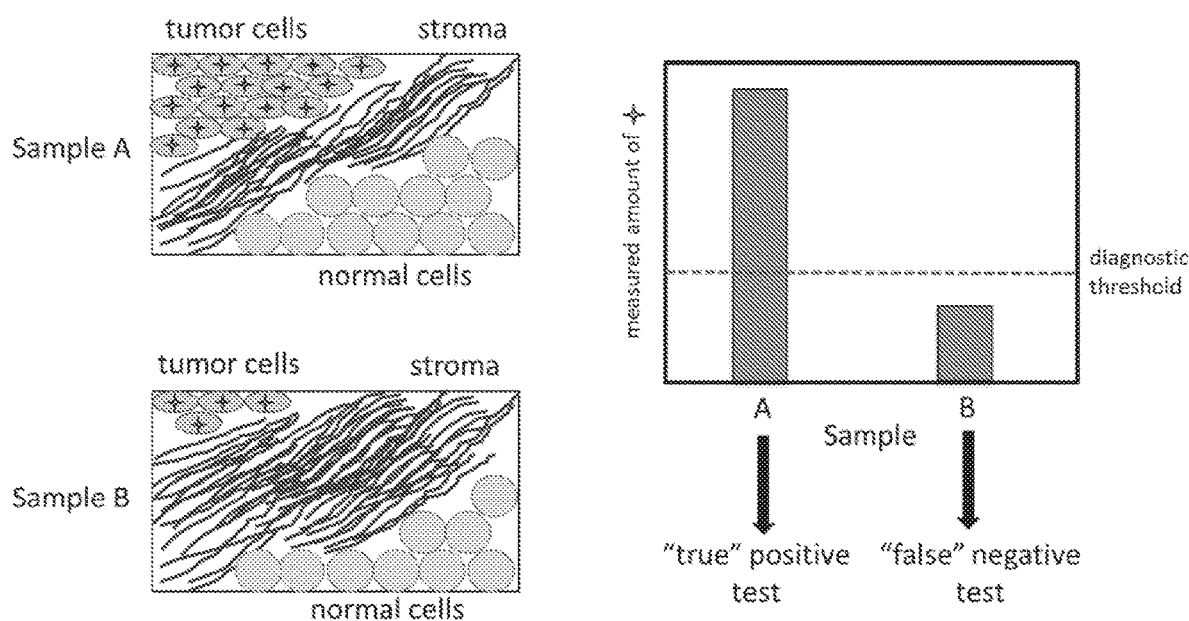
FIG. 1 provides an exemplary schematic representation of differences in cell component composition between two different heterogeneous biospecimens (Sample A and Sample B) and exemplifies that differences in cell component composition between two biospecimens that contain tumor cells expressing a similar amount of a tumor cell target protein (✧) per cell can skew test results based on uncorrected measurement of the target protein in each sample.
Figure 2:
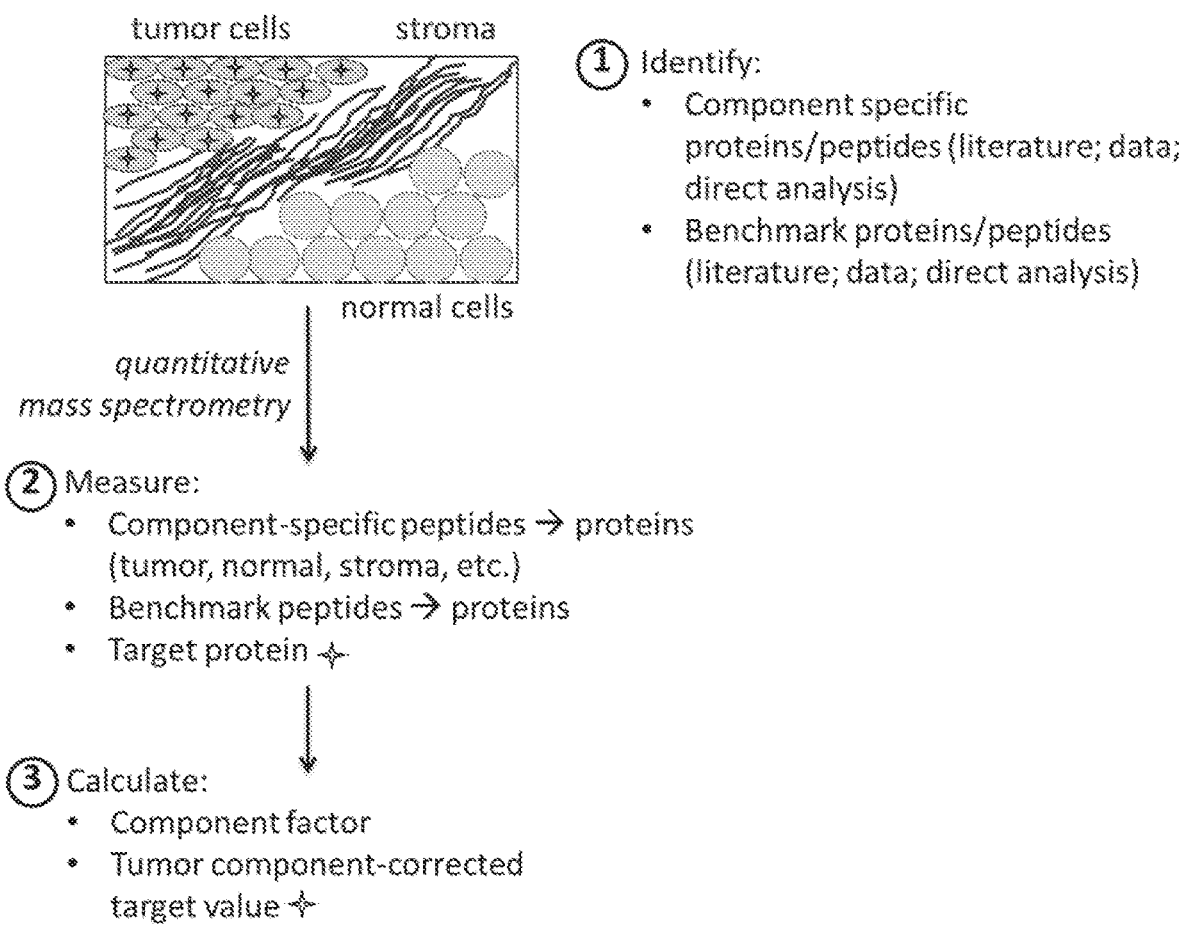
FIG. 2 provides a flow chart illustrating an exemplary embodiment of the disclosed methods.
Figure 3:
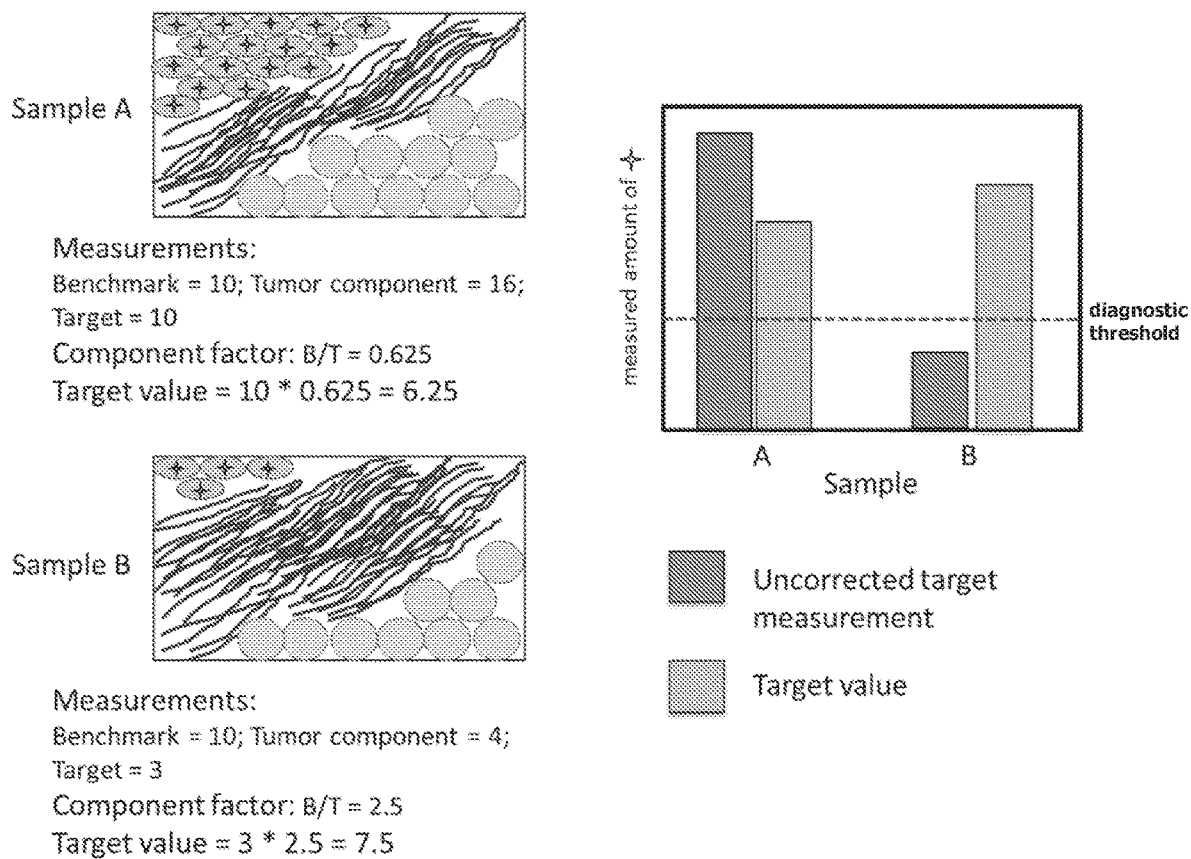
FIG. 3 provides an exemplary schematic representation of corrected measurements of a tumor cell target protein (✧) in two different heterogeneous biospecimens (Sample A and Sample B) according to an embodiment of the disclosed methods.
Figure 4:
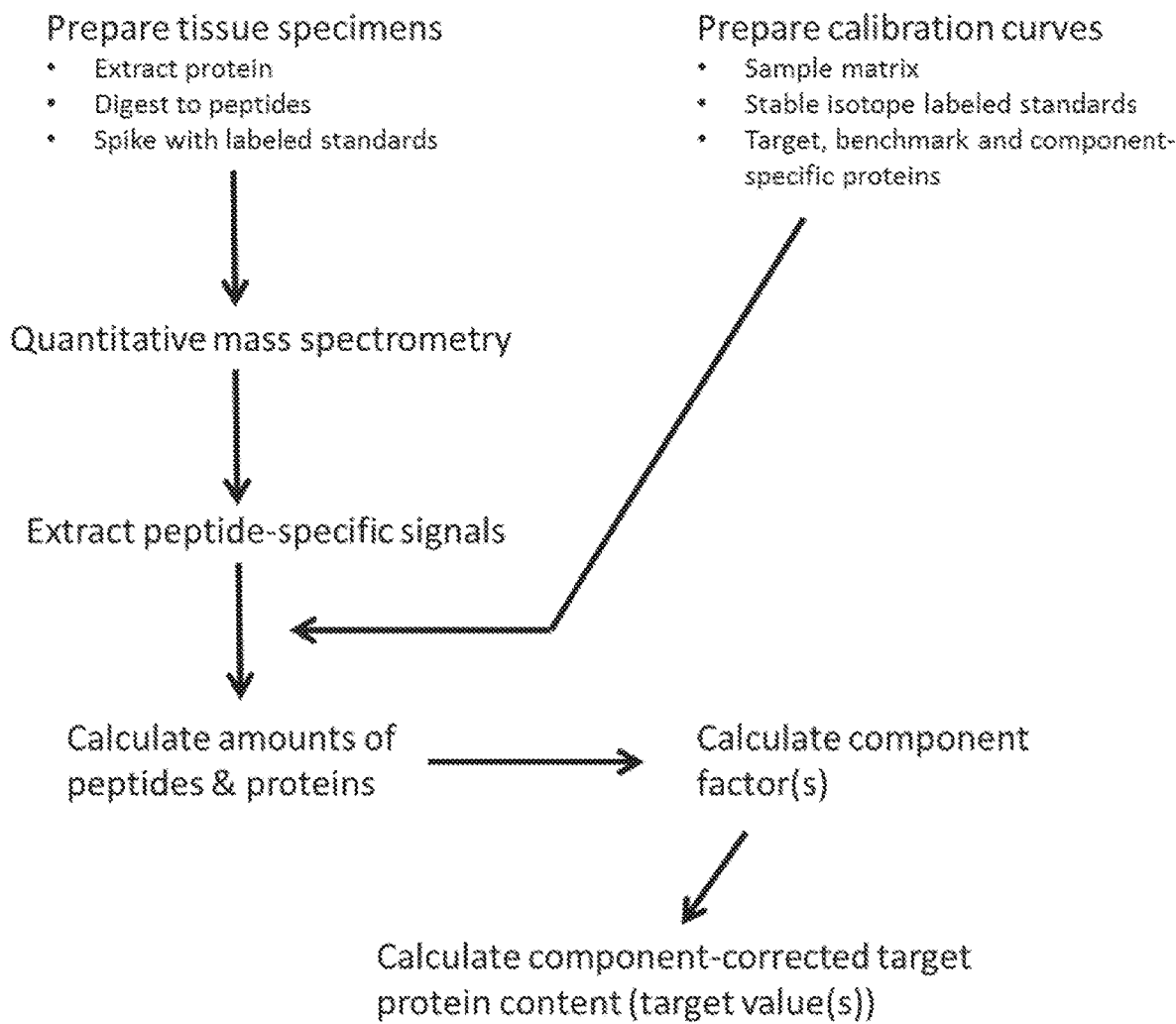
FIG. 4 provides a flow chart illustrating an exemplary embodiment of the disclosed methods.

Analysis by mass spectrometry (MS) provides a powerful new alternative to IHC for the measurement of proteins in tissues. For MS analyses, a tissue specimen may be homogenized and subjected to protein extraction, and the extracted proteins may be digested using enzymatic or chemical reagents to form peptides, which are then analyzed by tandem mass spectrometry techniques known as selected reaction monitoring (SRM), multiple reaction monitoring (MRM) or parallel reaction monitoring (PRM), depending on the specific type of MS instrument used. Peptides are selectively detected by monitoring sequence-specific fragmentations. Targeted measurement of proteotypic peptide sequences specific to proteins provides a universal means to systematically configure sensitive, specific assays. Moreover, a single SRM/MRM/PRM analysis can monitor up to approximately 100 proteins. MS-based protein assays thus offer the potential to systematically implement diagnostic tests with a specificity, sensitivity, and information content that far exceeds the capacity of IHC.

Other protein assay techniques can be used to measure proteins in biospecimens or protein extracts derived from biospecimens. Such assays include immunoassays, most commonly enzyme-linked immunosorbent assays (ELISAs) and newer variations of ELISAs. The availability of nucleic acid aptamers also enables sensitive, specific measurement of proteins with aptamer-based affinity reagents. Mass spectrometry of intact (undigested) proteins ("top down" analysis) is emerging as an alternative method to the analysis of proteolytically cleaved proteins and enables selective measurement of intact proteins and their various modified forms.

A key barrier to the implementation of protein quantitation for analysis of tissue proteins based on MS and other protein quantification techniques is the problem of heterogeneity of tissue specimens, which contain multiple cell types and stroma in varying proportions from specimen to specimen. Whereas IHC is performed in the context of microscopic examination of a tissue's cellular composition, analyses by MS, ELISA, and aptamer-based methods involve homogenization of specimens, which precludes observation of the spatial cellular organization and composition of the specimens. Thus, a targeted MS analysis of a tumor cell-specific protein, for example, will yield measurements that are dramatically influenced not only by the expression of the protein in the tumor cells, but also by the proportion of tumor cells compared to other cell types and stroma in each specimen. The same challenge applies to other biospecimens, including small biopsies, exfoliated cell mixtures, and cell populations collected from blood and other biofluids. Thus, a key problem to be solved in MS-based protein analysis of heterogeneous multicellular biospecimens is to overcome the bias introduced by variability in cell-type composition.

The present disclosure provides methods to perform precise, accurate measurements of proteins in heterogeneous multicellular biospecimens, in which the cellular and stromal composition often varies substantially between individual specimens. A protein target is typically expressed in a particular cell type in a tissue sample or other biospecimen. Although the diagnostic test is intended to determine the abundance of the target protein in the cell type of interest, a major source of variation is the proportion of the cells of interest as a fraction of all cell types and stroma in each specimen. Thus, a protein that is highly abundant in cells that comprise only a small fraction of the specimen will yield a low value upon measurement. A diagnostic test result for that target protein would thereby yield an erroneous result based on the low value. On the other hand, a measured value for the target protein that corrects for the low proportion of its cells of origin in the specimen would provide a reliable, accurate result and a more clinically useful interpretation.

The disclosed methods achieve correction for cell composition of a biospecimen through the use of measurements for proteins that are characteristically expressed in different cell types present in a biospecimen. This approach is supported by data to demonstrate that different cell types and stroma in biospecimens, such as, for example, tumor specimens, indeed contain proteins that are selectively expressed in particular cell populations of the heterogeneous biospecimen, such as in stroma or in neoplastic cells of human breast and colon cancers. These component-specific proteins are thus measured in a multiplexed assay, such as an MS assay, immunoassay, or aptamer-based assay, along with the target proteins whose measurement is the objective of the analysis. Because measurements of the component-specific proteins and the target proteins must be normalized for the amount of total protein in each specimen, benchmark proteins are also incorporated into the assay. Different benchmark proteins may be selected for each different biospecimen type, and preferably have low variation in abundance, regardless of the cellular and stromal composition of the particular biospecimen. The disclosure includes analytical methods for incorporating these measurements to compute a cell component factor for each specimen, against which the abundance of the target proteins is normalized.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are hereby incorporated by reference in their entirety. The materials, methods, and examples disclosed herein are illustrative only and not intended to be limiting.

"About" is used synonymously herein with the term "approximately." Illustratively, the use of the term "about" indicates that values slightly outside the cited values, namely, plus or minus 10%. Such values are thus encompassed by the scope of the claims reciting the terms "about" and "approximately."

"Administer," "administering," "administered," or "administration," as used herein, refer to any manner of providing a drug compound or a pharmaceutical composition (e.g., one described herein), to a subject or patient. Routes of administration can be accomplished through any means known by those skilled in the art. Such means include, but are not limited to, oral, buccal, intravenous, subcutaneous, intramuscular, transdermal, by inhalation and the like.

"Benchmark protein," as used herein, refers to a protein that is expressed at substantially uniform abundance across multiple heterogeneous biospecimens of the same type, independent of the particular cell type composition of each individual heterogeneous biospecimen. A benchmark protein has substantially similar abundance in all cell type components of the biospecimen.

"Biospecimen," as used herein, refers to a biological sample comprising cells. A biospecimen may be obtained from a subject. A biospecimen may comprise, for example, cultured cells; a tissue sample; a biopsy; a needle biopsy; a tumor sample; a biofluid such as blood; xenograft tissue such as tumor xenograft tissue; exfoliated cells such as buccal mucosa, urinary tract epithelium, airway epithelium, or gastrointestinal tract epithelium; or any other biological sample of interest. Biospecimens may be obtained through methods familiar to those of ordinary skill in the art.

"Component factor," as used herein, refers to calculated adjustment factor based on the proportion of proteins in a heterogeneous biospecimen that are from a particular component cell type of interest.

"Component-specific protein," as used herein, refers to a protein whose expression is unique to or substantially enriched in a particular cell type or stromal component in a heterogeneous biospecimen compared to other cell types present in the heterogeneous biospecimen.

"Comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

"Contacting" as used herein, e.g., as in "contacting a sample" refers to contacting a sample directly or indirectly in vitro, ex vivo, or in vivo (i.e. within a subject as defined herein). Contacting a sample may include addition of a compound to a sample (e.g., a sample of proteins extracted from a biospecimen), or administration to a subject. Contacting encompasses administration to a solution, cell, tissue, mammal, subject, patient, or human. Further, contacting a cell includes adding an agent to a cell culture.

"Effective amount," as used herein, refers to a dosage or an amount of a compound or a composition effective for eliciting a desired effect. This term as used herein may also refer to an amount effective at bringing about a desired in vivo effect in an animal, e.g., a mammal, e.g., a human. For example, in methods of treating cancer, an effective amount may be an amount sufficient to treat the disorder.

"Proteotypic," as used herein, refers to peptide sequences that are uniquely present in the protein from which they are derived in that organism and thus represent evidence that measurements of the proteotypic peptide represent only the parent protein and not other proteins present in that organism.

"Subject," as used herein, refers to human and non-human animals. Exemplary human subjects include a human patient having a disorder, e.g., cancer, or a normal subject. The term "non-human animals" includes all vertebrates, e.g., non-mammals (such as chickens, amphibians, reptiles) and mammals, such as non-human primates, domesticated and/or agriculturally useful animals (such as sheep, dogs, cats, cows, pigs, etc.), and rodents (such as mice, rats, hamsters, guinea pigs, etc.).

"Target protein," as used herein, refers to a protein of interest to be measured in a heterogeneous biospecimen. The amount of a target protein expressed by at least one cell type in a biospecimen may vary between heterogeneous biospecimens obtained from different subjects or from the same subject at different times or different anatomical locations. In some embodiments, a target protein may be the target of a drug or other therapies or a protein that modifies drug responses. In some embodiments, a target protein may be a protein identified or hypothesized to serve as a biomarker to predict or detect responses to therapy, to predict or detect risk of metastasis or other biological properties, or to assess disease prognosis or other clinical outcomes.

"Treat" or "treating" or "treatment" directed to a subject having a disorder, as used herein, refers to administering a compound or a composition described herein to the subject, such that at least one symptom of the disorder is cured, healed, alleviated, relieved, altered, remedied, ameliorated, or improved. Treating includes administering an amount of a compound or a composition to effective to alleviate, relieve, alter, remedy, ameliorate, cure, improve or affect the disorder or the symptoms of the disorder. The treatment may inhibit deterioration or worsening of a symptom of a disorder.

2. METHODS FOR PROTEIN ANALYSIS

In one embodiment, the disclosed methods can be used to measure the abundance of one or more carcinoma cell-specific proteins in a tumor that contains one or more other cell types, such as normal epithelium, smooth muscle, immune cells, and stroma. In breast and colon carcinomas, for example, the proportion of carcinoma cells ranges from 10 to 90 percent, with the balance of a given tumor tissue specimen containing stroma and other cell types in varying proportions. Uncorrected measurement of a target protein present at similar or equal abundance in the carcinoma cells in different specimens would yield a higher value in a tumor tissue specimen with a high fraction of carcinoma cells than in a tumor tissue specimen with a low fraction of carcinoma cells. Determination of a component factor corrected amount of the target protein as disclosed herein eliminates or mitigates measurement bias due to differences in cell and stroma composition between the specimens.

In another embodiment, the disclosed methods permit accurate measurement of target proteins in xenograft tumor models, which are widely used in oncology drug development. Xenograft models are characterized by human neoplastic cells grown in another host species (typically mice). Although the target proteins to be measured are present in the human xenograft-derived cell component, xenograft specimens obtained from the host will also contain mouse host proteins in varying proportions. In some embodiments, the component-specific protein can be a non-human host species protein to allow calculation of a component factor of non-human host cells in a xenograft specimen. In some embodiments, the component-specific protein may be a human protein to allow calculation of a component factor of a human xenograft-derived cell component in a xenograft specimen.

In another embodiment, the disclosed methods permit accurate measurement of target proteins in heterogeneous mixtures of cells, which may be collected, for example, as tissue biopsies. Like larger tissue specimens, these small biopsy specimens have variable, heterogeneous cell content, such as cancerous cells and normal cell types, but assessment of small biopsy composition by microscopy and IHC-based techniques is not possible. Quantifying the amount of one or more component-specific proteins may establish the cell composition of the biopsy specimen and may enable correction of measurements for target proteins as described for other biospecimens.

In another embodiment, the disclosed methods permit accurate measurement of target proteins in cell populations obtained from blood or other biofluids. Component-specific protein measurements may enable quantification of distinct cell populations, such as lymphocyte, leukocyte, macrophage, or monocyte cell populations through cell component specific proteins. Such measurements may be used to calculate a component factor for any of the distinct cell populations, thereby enabling normalization of measurement for target proteins that are specific to any of the cell component populations.

In another embodiment, the disclosure permits accurate measurement of target proteins in exfoliated cell populations obtained, for example, from buccal mucosa, urinary tract epithelium, airway epithelium, or gastrointestinal tract epithelium. Cell component-specific protein measurements could enable quantification of distinct epithelial cell populations through measurement of component-specific proteins. Such measurements can be used to calculate component factors for these a cell component population, thereby enabling normalization of measurement for target proteins that are specific to a component cell population.

In another embodiment, the disclosure permits accurate assessment of the infiltration of a biospecimen—such as a carcinoma tumor sample or other neoplastic tissue sample—by immune cells. For example, a component-specific protein indicative of T cells may include an established T cell marker (e.g., CD4 and CD8) or other immune cell component-specific protein. The component factor(s) calculated for one or more immune cell types in a biospecimen enables quantitative assessment of immune infiltration.

One or more component-specific proteins may be identified for one or more component cell types in a heterogeneous biospecimen. For example, cancer-cell specific proteins, carcinoma specific proteins, normal epithelial specific proteins, smooth muscle specific proteins, or stroma specific proteins may be used as component-specific proteins in embodiments of the disclosed methods. Component-specific proteins may be selected based on data obtained by mass spectrometry analysis of cell components collected from a biospecimen by laser capture microdissection.

Embodiments of this disclosure may involve the measurement of peptides of one or more target proteins, one or more component-specific proteins, and one or more benchmark proteins. These proteins and their proteotypic peptides may be selected and analyzed according to the following procedures.

A biospecimen of interest may be obtained from any desired source using methods and techniques familiar to those of ordinary skill in the art. Proteins may be extracted from a biospecimen using techniques known to those of ordinary skill in the art, such as by acid precipitation, organic solvent precipitation, extraction with detergents or aqueous and organic solvent mixtures, among others. Extraction may employ methods of cell and tissue disruption, including sonication, cryopulverization, mechanical disruption with beads, and extrusion through membranes. Proteins may be extracted using techniques that yield total protein samples representative of all proteins present in the biospecimen, or in some embodiments, extraction techniques may be used that result in more selective representation of proteins in the biospecimen, such as fractionation techniques that include, for example, selection or enrichment of proteins within a desired molecular weight range or isoelectric point range or based on physical characteristics, such as hydrophobicity. In some embodiments, proteins may be captured through affinity binding to one or more other molecules, such as a protein, an antibody, a small molecule probe, a lectin, or a nucleic acid aptamer. In some embodiments, proteins may be analyzed in a biospecimen without performing an extraction procedure, such as, for example, when the biospecimen comprises a biofluid.

In some embodiments, proteins may be cleaved to form peptides by any suitable approach known in the art. For example, the proteins may be cleaved by contacting the proteins with a proteolytic enzyme, such as, for example, one or more of trypsin, chymotrypsin, endoproteinase Asp-N, endoproteinase Lys-C, endoproteinase Glu-C, and subtilisin. In some embodiments, the proteins may be cleaved using a chemical reagent, such as, for example, cyanogen bromide.

A target protein may be, for example, a target of a drug or other therapy, a protein that modifies a drug response, or a protein identified or hypothesized to serve as a biomarker to predict or detect a response to a therapy, a risk of metastasis or other biological property, or to assess a disease prognosis or other clinical outcome. Diseases of interest may include neoplasms, tumors, or cancers, such as carcinomas; immune-mediated diseases such as rheumatoid arthritis; immune inflammatory disorders; metabolic diseases; or any other disease or disorder of interest. A target protein may be selected from public or proprietary data or prior knowledge or hypotheses regarding its role as a target of a therapeutic or as a modulator of response to a therapeutic or as a contributor to a phenotypic characteristic of a disease, tumor, or metastasis. A target protein may be selected by analysis of DNA, RNA, or protein from a biospecimen associated with a disease of interest, such as a cancer, or from a cellular or xenograft model of a disease. A target protein also may be selected by computational analysis or modeling of a biological system, including a biological network, interactome, pathway, or cellular or extracellular system component, such as an organelle or extracellular matrix. In some embodiments, a target protein may be a sequence variants resulting from single nucleotide DNA sequence polymorphisms, somatic DNA mutations, insertions, deletions or chromosomal rearrangements. In some embodiments, a target protein may be a sequence variant generated during RNA processing.

A component-specific protein may be identified as a protein whose expression is unique to or substantially enriched in a cell or stromal component of interest compared to other cell components of a biospecimen. In a biospecimen, the abundance of a component-specific protein may be proportional to the fraction of the cell component of interest in the biospecimen. Enrichment of a component-specific protein can be inferred from public or proprietary data or prior knowledge or hypotheses, but preferably may be experimentally verified by direct analysis of the component-specific protein in a sample of the biospecimen of interest. Experimental verification may include immunohistochemistry analysis with a highly specific antibody, and/or laser capture microdissection of specific cellular or stromal components followed by mass spectrometry-based quantitative analysis of proteotypic peptides from a proteolytic digest of the captured material.

A benchmark protein may be identified as a protein that is expressed at uniform or consistent or substantially uniform or consistent abundance across multiple samples of a particular type of biospecimen of interest, independent of the cellular and stromal composition of each individual sample. A benchmark protein also may be identified as having similar abundance in all cellular and stromal components of a biospecimen. The uniformity of abundance of a benchmark protein can be inferred from public or proprietary data or prior knowledge or hypotheses, but preferably may be experimentally verified by direct analysis of the benchmark protein in samples of the biospecimen of interest. Experimental verification may include immunohistochemistry analysis with a highly specific antibody, and/or laser capture microdissection of multiple cellular or stromal components followed by mass spectrometry-based quantitative analysis of proteotypic peptides from a proteolytic digest of the captured material.

An exemplary formula for the application of benchmark, component-specific and target protein measurements to produce a component-adjusted target value is:

Target value=$T*B/C$

Where T is the measured amount for a target protein; where B is the measured amount for a benchmark protein; and where C is the measured amount for a component-specific protein.

In some embodiments, cleaved peptides may be analyzed by liquid chromatography-tandem mass spectrometry. For example, peptides may be analyzed without initial fractionation or may initially be fractionated by ion exchange chromatography, by high pH reverse phase chromatography, by hydrophilic interaction chromatography or by isoelectric focusing. The peptide fractions or mixtures then may be analyzed by reverse phase liquid chromatography coupled to electrospray tandem mass spectrometry. Several tandem mass spectrometry instruments are commonly used, including ion trap, Orbitrap, time of flight, triple quadrupole, hybrid quadrupole-Orbitrap, hybrid quadrupole-time of flight, ion mobility and ion cyclotron resonance mass spectrometers. These analyses record full-scan mass spectra of peptide ions, which may include high-resolution scans capable of indicating isotopic composition and charge states of the peptide ions. Fragmentation of the peptide ions by collision-induced dissociation, high energy collision-induced dissociation, electron transfer dissociation, electron capture dissociation, and infrared multiphoton dissociation produces tandem mass spectra, which represent energetic cleavages of the peptide ions along the peptide sequence. Peptide sequences encoded by the tandem mass spectra can be identified by database search algorithms and software through procedures that are familiar to those of ordinary skill in the art.

Quantitative measurements of proteotypic peptides can be made by targeted measurement of peptide ions and their fragments in tandem mass spectrometry. Such methods may include selected reaction monitoring, multiple reaction monitoring, or parallel reaction monitoring, depending on the type of tandem mass spectrometer used. With heavy isotope-labeled peptide standards and calibration curves, accurate and precise quantitation of proteotypic peptides can be achieved.

Proteotypic peptides may be selected for a target protein, a benchmark protein, or a component specific protein using criteria for proteotypic peptide selection known to those of ordinary skill in the art. For example, approaches may be used to select a proteotypic peptide to be measured in a spectrometry-based assay may include, for example, the use of bioinformatics, prediction algorithms, and mining of empirical data. One advantage of selecting proteotypic peptides using empirical mass spectrometry data is that such peptides are known to be detectable, which therefore increases the success of subsequent MS-based assays. Guidelines for selecting a proteotypic peptide may include selecting a peptide that is unique to a single gene product and selecting a peptide that is observable by mass spectrometry are the most prevalently used filtering criteria. In some embodiments, criteria regarding optimal peptide length, hydrophobicity, and exclusion of reactive amino acid residues may also be used in proteotypic peptide selection.

An exemplary formula for the MS-based application of benchmark, component-specific, and target protein measurements to produce a component-adjusted target value is:

Target value=$(T1+T2+\ldots+Tn)*(B1+B2+\ldots+Bn)/(C1+C2+\ldots+Cn)$

Wherein T1, T2, . . . Tn are the measured amounts for one or more proteotypic peptides from a target protein; where B1, B2, . . . Bn are the measured amounts for one or more proteotypic peptides from one or more benchmark proteins; and where C1, C2, . . . Cn are the measured amounts for one or more proteotypic peptides from one or more component-specific proteins.

In some embodiments, a formula for the MS-based application of benchmark, component-specific, and target protein measurements to produce a component-adjusted target value may be:

Target value=$(t1T1+t2T2+\ldots+tnTn)*(b1B1+b2B2+\ldots+bnBn)/(c1C1+c2C2+\ldots+cnCn)$ Wherein T1, T2, . . . Tn are the measured amounts for one or more proteotypic peptides from a target protein; where B1, B2, . . . Bn are the measured amounts for one or more proteotypic peptides from one or more benchmark proteins; where C1, C2, . . . Cn are the measured amounts for one or more proteotypic peptides from one or more component-specific proteins; where t1, t2, . . . tn are normalization factors to adjust for MS instrument response differences between the corresponding proteotypic peptides T1, T2, . . . Tn; where b1, b2, . . . bn are normalization factors to adjust for MS instrument response differences between the corresponding proteotypic peptides B1, B2, . . . Bn; and where c1, c2, . . . cn are normalization factors to adjust for MS instrument response differences between the corresponding proteotypic peptides C1, C2, . . . Cn.

In some embodiments, proteins may be analyzed by mass spectrometry of intact proteins. Although the most widely used approach to protein identification and quantitation by mass spectrometry is analysis of peptides produced by digestion of proteins, direct measurement and quantitation of intact proteins is also possible. This approach, which is termed "top down" analysis, typically employs electrospray ionization to generate protein ions in the source of a Fourier transform ion cyclotron resonance, an ion trap or an Orbitrap mass spectrometer. The protein ions then are fragmented either by electron transfer dissociation or electron capture dissociation and the peptide fragment sequences are identified by tandem mass spectrometry. The key advantage of the top down approach is the analysis of distinct modified forms of proteins by systematic fragmentation of the intact molecules. In contrast to mass spectrometry analyses of protein digests, measurements of proteins in "top down" analyses are based on signals for the intact proteins.

For example, analyses of benchmark, component-specific, and target proteins may be achieved by extracting proteins from a biospecimen and then performing a top down mass spectrometry assay on an aliquot of the extract. A generalized exemplary formula for the application of benchmark, component-specific, and target protein top down mass spectrometry assay measurements to produce a component-adjusted target value is:

$$\text{Target value} = (tT)*(bB)/(cC)$$

Where T is the measured signal from the target protein; where B is the measured signal for a benchmark protein; where C is the measured signal for a component-specific protein; where t is a normalization factor to adjust for MS instrument response to the target protein; where b is a normalization factor to adjust for MS instrument response to the benchmark protein; and where c is a normalization factor to adjust for MS instrument response to the component-specific protein.

In some embodiments, proteins may be analyzed by immunoassay, which is the most widely used method to quantify proteins in biology and medicine. Protein detection in immunoassays is achieved by binding of a specific antibody to the protein of interest in the particular assay. The most widely used immunoassay format is the enzyme-linked immunosorbent assay (ELISA), in which an antibody ("capture antibody") is immobilized on a particle or surface. Upon binding of the protein of interest, the complex may be detected, for example, with a second antibody ("detection antibody") labeled with an enzyme, which produces a product that can be detected by spectrophotometry, fluorimetry, electrochemistry, or other analytical technique. In some embodiments, the detection antibody may be contacted with a detectably labeled secondary reagent (such as another antibody) that binds to the detection antibody itself or binds to a label bound to the detection antibody (such as streptavidin binding to a biotinylated detection antibody). Through use of an authentic standard and calibration curve, the assay may be used to quantify the protein of interest. Such methods are known as "sandwich ELISA." An alternative to the sandwich ELISA is the "competitive ELISA," in which a single capture antibody is immobilized and the protein of interest binds in competition with a labeled version of the protein of interest. Quantitation is achieved with a standard of the protein of interest and a calibration curve. Multiplexed immunoassay analysis (simultaneous measurement of multiple proteins) can be achieved with several commercially produced, automated analyzer systems.

Analyses of benchmark, component-specific, and target proteins may be achieved by extracting proteins from a biospecimen and then performing a sandwich ELISA on an aliquot of the extract. Each assay may include capture and detection antibodies that are specific for a protein of interest, such as a benchmark protein, a component-specific protein, or a target protein. A calibration curve is prepared to enable quantitation of detected proteins.

A generalized formula for the application of benchmark, component-specific and target protein immunoassay measurements to produce a component-adjusted target value is:

$$\text{Target value} = T*B/C$$

Where T is the measured amount for the target protein; where B is the measured amount for a benchmark protein; and where C is the measured amount for a component-specific protein.

In some embodiments, proteins may be analyzed by aptamer-based assays. Aptamers are single-stranded nucleic acid polymers that selectively recognize target molecules through binding interactions with the stable, folded aptamer structures. Aptamers may be DNAs, RNAs or analogous polymers synthesized from modified purine and pyrimidine bases. Typically produced from libraries of nucleotide sequences that are selected by binding to a molecular target, aptamers are the nucleic acid equivalent of antibodies. However, the ability to determine exactly the sequence of target-binding aptamers makes possible both the systematic refinement and exact reproduction of these reagents. Aptamer-based analyses are analogous to immunoassays, in that recognition of a target protein by the reagent is followed by isolation and detection of the aptamer-protein complex. Aptamer-based protein analyses can yield quantitative measurements of proteins and can be multiplexed.

Analyses of benchmark, component-specific, and target proteins may be achieved by extracting proteins from a biospecimen and then performing an aptamer assay on an aliquot of the extract. Each assay requires aptamer molecules that are specific for the protein analyte. A calibration curve is prepared to enable quantitation of the detected proteins.

An exemplary generalized formula for the application of benchmark, component-specific, and target protein aptamer assay measurements to produce a component-adjusted target value is:

$$\text{Target value} = T*B/C$$

Where T is the measured amount for the target protein; where B is the measured amount for a benchmark protein; and where C is the measured amount for a component-specific protein.

3. EXAMPLES

The disclosed compounds, compositions, processes, and methods will be better understood by reference to the following examples, which are intended as an illustration of and not a limitation upon the scope of the invention.

Example 1

Protein Extraction from Frozen Tissue

Tissue samples were washed prior to digestion to eliminate any residual optimal cutting temperature compound (OCT). The tissue was placed in a 1.5 mL micro-tube and washed with 1 mL 70% ethanol/30% $H_2O$ for 30 seconds with vortexing. The supernatant was then discarded and the tissue washed with 1 mL of 100% $H_2O$ for 30 seconds with vortexing and again the supernatant was discarded. One milliliter of 70% ethanol/30% $H_2O$ was added to the tissue sample and incubated for 5 min at room temperature followed by centrifugation at 20000×g for 2 minutes at 20° C. The supernatant was removed and this wash step was repeated. Next, 1 mL of 85% ethanol/15% $H_2O$ was added to the tissue and incubated for 5 minutes at room temperature followed by centrifugation at 20000×g for 2 minutes at 20° C. The supernatant was removed and this wash step was repeated. For the final wash step, 1 mL 100% ethanol as added to the tissue and incubated for 5 minutes at room temperature followed by centrifugation at 20000×g for 2 minutes at 20° C. The supernatant was removed the final wash step was repeated.

Following OCT removal, tissue specimens were placed in 1.5 mL micro-centrifuge tubes and re-suspended 100 μL of trifluoroethanol (TFE) and 100 μL of 100 mM ammonium bicarbonate, pH 8. If additional buffer was required, equal volumes of TFE and 100 mM ammonium bicarbonate pH 8.0, could be added accordingly. Samples were sonicated for 20 seconds followed by a 30-second incubation on ice. This sonication step was repeated two additional times making sure samples were placed on ice between sonications. The resulting homogenate was heated with shaking at 1000 rpm for 1 hour at 60° C. followed by a second series of sonication steps, as described above. At this point, a protein measurement was obtained using a BCA Protein Assay (Thermo Fisher Scientific) using the manufacturer's protocol.

Example 2

Protein Extraction from Formalin-Fixed, Paraffin-Embedded Tissue

Paraffin was removed with three washes in 1 ml of Sub-X clearing medium (Leica Biosystems), and rehydration was achieved with three washes each in 1 ml of 100%, 85%, and 70% ethanol. Tissue was then resuspended in 100 μl of ammonium bicarbonate (100 mM, pH 8.0) either alone or with 1 mM EDTA or 100 mM pyridoxamine. Samples were then heated at 80° C. for 2 hours. Trifluoroethanol (100 μl) was then added, and the samples were sonicated for 20 seconds followed by 30 second incubation on ice. The sonication was repeated twice. The resulting homogenate was heated for 1 h at 60° C. followed by a second series of sonication steps, as stated above. At this point, a protein measurement was obtained using a BCA Protein Assay (Thermo Fisher Scientific) using the manufacturer's protocol.

Example 3

Digestion of Proteins to Tryptic Peptides

Based upon the BCA protein measurements, the required amount of protein was aliquoted and reduced with tris(2-carboxyethyl)phosphine (TCEP, 20 mM) and dithiothreitol (DTT, 50 mM) at 60° C. for 30 minutes followed by alkylation with iodoacetamide (IAM, 100 mM) in the dark at room temperature for 20 min. The lysate was diluted with the appropriate volume of 50 mM ammonium bicarbonate, pH 8.0, to reduce the TFE concentration to 10%, trypsin was added at a ratio of 1:50 (w:w), and digestion was allowed to proceed overnight at 37° C. The digested mixture was frozen at −80° C. and lyophilized to dryness. The lyophilized samples were re-suspended in 350 μL of HPLC-grade water, vortexed vigorously for one minute, and desalted using an Oasis HLB 96-well μElution plate (30 μm, 5 mg, Waters Corp., Milford, MA), which were pre-washed with 500 μL of acetonitrile and equilibrated with 750 μL of HPLC-grade water. The flow-through was discarded and the plates were washed with 500 μL of HPLC-grade water and the peptides eluted with 80% acetonitrile and dried in vacuo. Samples were stored in the freezer prior to further analysis.

Example 4

Protein Preparation from Laser Capture Microdissected (LCM) Specimens

For LCM, tumor tissue was sectioned at 6 μm in a Leica CM 1850 Cryostat (Leica Microsystems GmbH, Wetzlar, Germany). The sections were mounted on uncharged glass slides without the use of embedding media and placed immediately in 70% ethanol for 30 seconds. Subsequent dehydration was achieved using graded alcohols and xylene treatments as follows: 95% ethanol for 1 minute, 100% ethanol for 1 minute (twice), xylene for 2 minutes, and second xylene 3 minutes. Slides were then dried in a laminar flow hood for 5 minutes prior to micro-dissection. Sections were then laser captured micro-dissected with PixCell II LCM system (Arcturus Engineering). Approximately 10,000 cells per cap of were acquired at up to 5,000 shots with a 30 μm diameter laser beam.

For isolation of proteins from LCM-collected tissue, all membranes containing the micro-dissected cells from tumor tissue were removed and placed directly into a 1.5 mL Eppendorf tube and processed using SDS-PAGE. Membranes containing the micro-dissected cells were suspended in 25 μL of SDS sample buffer and 10 μL water, reduced with 5 μL 500 mM dithiothreitol, and heated in a 70-80° C. water bath for approximately 10 min. The supernatant was then electrophoresed approximately 2 cm into a 4-12% Bis-Tris gel, stained with Colloidal Blue, and destained with water.

The full 2 cm gel regions were excised and washed with 100 mM ammonium bicarbonate for 15 minutes. The liquid was discarded and replaced with fresh 100 mM ammonium bicarbonate, and the proteins were reduced with 5 mM dithiothreitol for 20 minutes at 55° C. After cooling to room temperature, iodoacetamide was added to 10 mM final concentration, and the samples were placed in the dark for 20 minutes at room temperature. The solution was discarded and the gel pieces were washed with 50% acetonitrile/50 mM ammonium bicarbonate 20 minutes, followed by dehydration with 100% acetonitrile. The liquid was removed and the gel pieces were completely dried, re-swelled with 0.5 μg of modified trypsin (Promega) in 100 mM $NH_4HCO_3$, and digested overnight at 37° C. Peptides were extracted by three changes of 60% acetonitrile/0.1% TFA, and all extracts were combined and dried in vacuo. Samples were reconstituted in 35 μL 0.1% formic acid for LC-MS/MS analysis.

Example 5

Mass Spectrometry Analyses

Peptide mixtures were resuspended in an appropriate volume of 2% acetonitrile/0.1% formic acid and analyzed by mass spectrometry by any of several methods.

For targeted analysis of specific peptides by multiple reaction monitoring (MRM), triple quadrupole instrumentation typically was used. Briefly, target precursor ions and respective product ions transitions were selected and used to develop a MRM method for candidate lists of peptides. Experiments can be performed in an unscheduled manner, in which all transitions are scanned over the entire length of the LC gradient. A more efficient approach, which allows a larger number of transitions to be monitored in a single analysis, was to use scheduled or timed acquisitions. Using LC retention time information of each peptide, the acquisition of data for a specific peptide was scanned only during a specified retention time window centered on the retention time of the peptide. In this manner, more scans can be collected for each peptide, thereby improving the quantitation. An appropriate volume of the peptide digest was injected onto the reversed phase column and analyzed by the mass spectrometry. Representative instrument operating parameters for a Thermo TSQ Vantage triple quadrupole instrument included a spray voltage of 1300 V, and a capillary temperature of 210° C. Q1 and Q3 unit resolution of 0.7 FWHM, Q2 Argon gas pressure of 1.5 mTorr, scan width of 0.005 m/z, and a dwell time of 10 ms. Data were acquired and collected in .raw files which were then analyzed using the Skyline software.

For targeted analysis of specific peptides by parallel reaction monitoring (PRM), a Q-Exactive hybrid quadrupole-Orbitrap mass spectrometer was used. A precursor ion isolation list for the peptides to be analyzed can be exported from Skyline software analyses of the proteins to be measured and the list of precursor m/z values to be targeted is imported into the Inclusion List. Retention times can also be included to perform a scheduled analysis in a similar manner described for MRM. The method was configured include one Full-SIM MS scan followed by 15 t-MS2 scan events. Unlike MRM analyses, only the precursor values were monitored and product ions were extracted from the data post-acquisition. Data were collected as a .raw file and analyzed using Skyline software.

Example 6

Calibration for Targeted Analysis by Stable Isotope Dilution

Calibration curves were generated to determine the amount of measured peptide targets in the samples analyzed by MRM and PRM analyses. This was accomplished using stable isotope dilution, in which a standard curve consisting of an on-column concentration range (e.g., 1 amol/µL to 100 fmol/µL) of synthetic 12C14N peptides was prepared by serial dilutions in a background sample matrix (e.g., tissue, plasma, etc.) and a constant concentration of the 13C15N-isotopically labeled peptides. The ratios of the peak areas of the 12C14N peptides to that of the 13C15N-isotopically labeled peptides were used to generate the calibration curve. The response curve could be used to determine the limit of detection and quantification of each peptide.

Peptide digests from tissue samples to be analyzed were spiked with the same level of 13C15N-isotopically labeled peptides used to prepare the calibration curve. The peak area ratio of the endogenous target peptide to the corresponding 13C15N-isotopically labeled peptide was used to calculate the amount of protein in the sample from the calibration curve.

Example 7

Data Analysis with Skyline

The open-source software application Skyline was used for method development, including the selection of peptides and fragmentation transitions to be monitored in MRM or PRM analyses. Skyline also provides the analysis system for integration of signals from all MRM and PRM datasets. Skyline is vendor-neutral software that facilitates easy data sharing and custom report creation. All peak area integrations were performed using Skyline. Processed data, which may include peak areas, peak heights and chromatographic parameters, were directly exported from Skyline to .csv files for further statistical analyses.

Example 8

Measurement of ERBB1 in Colon Carcinoma Specimens by Mass Spectrometry of Proteotypic Peptides In one embodiment, the disclosed methods were used to measure the abundance of the protein ERBB1 (epidermal growth factor receptor), which is the target of the therapeutic drug cetuximab in treatment of certain colorectal cancers.

Benchmark proteins were identified for colorectal carcinomas. Benchmark proteins in colorectal carcinomas were identified from the dataset described by Zhang et al., *Proteogenomic characterization of human colon and rectal cancer*, Nature 513:382-387 (2014), and included proteins displaying less than 10% variation in abundance across the collection of 95 tumors described. Benchmark proteins identified in this way include ACTB, TUBA4A, IQGAP1, RPS3, AP1B1, EIF3K, and WASF2.

Component-specific proteins were selected based on data obtained by mass spectrometry analysis of the carcinoma cell component collected from 18 colorectal tumors by laser capture microdissection. Carcinoma cell component-specific proteins identified in this way create a "carcinoma cell signature" of 46 proteins (BCAP31, CCT4, CCT6A, CYC1, DARS, DDX3X, DHX15, ECH1, EIF4A3, FASN, HNRNPA3, HNRNPAB, HNRNPL, HSD17B4, ILF3, IMMT, KARS, KHDRBS1, LGALS3BP, LRPPRC, PA2G4, PABPC1, PAICS, PRDX5, PSMA6, PSMA7, RAB14, RABSC, RALY, RBMX, RHOA, RPL26, RPL28, RPL9, RPN2, RUVBL1, SF3B3, SHMT2, SLC12A2, SRSF1, SSB, TFRC, TMPO, TOP1, VDAC1, VDAC3).

Figure 5:
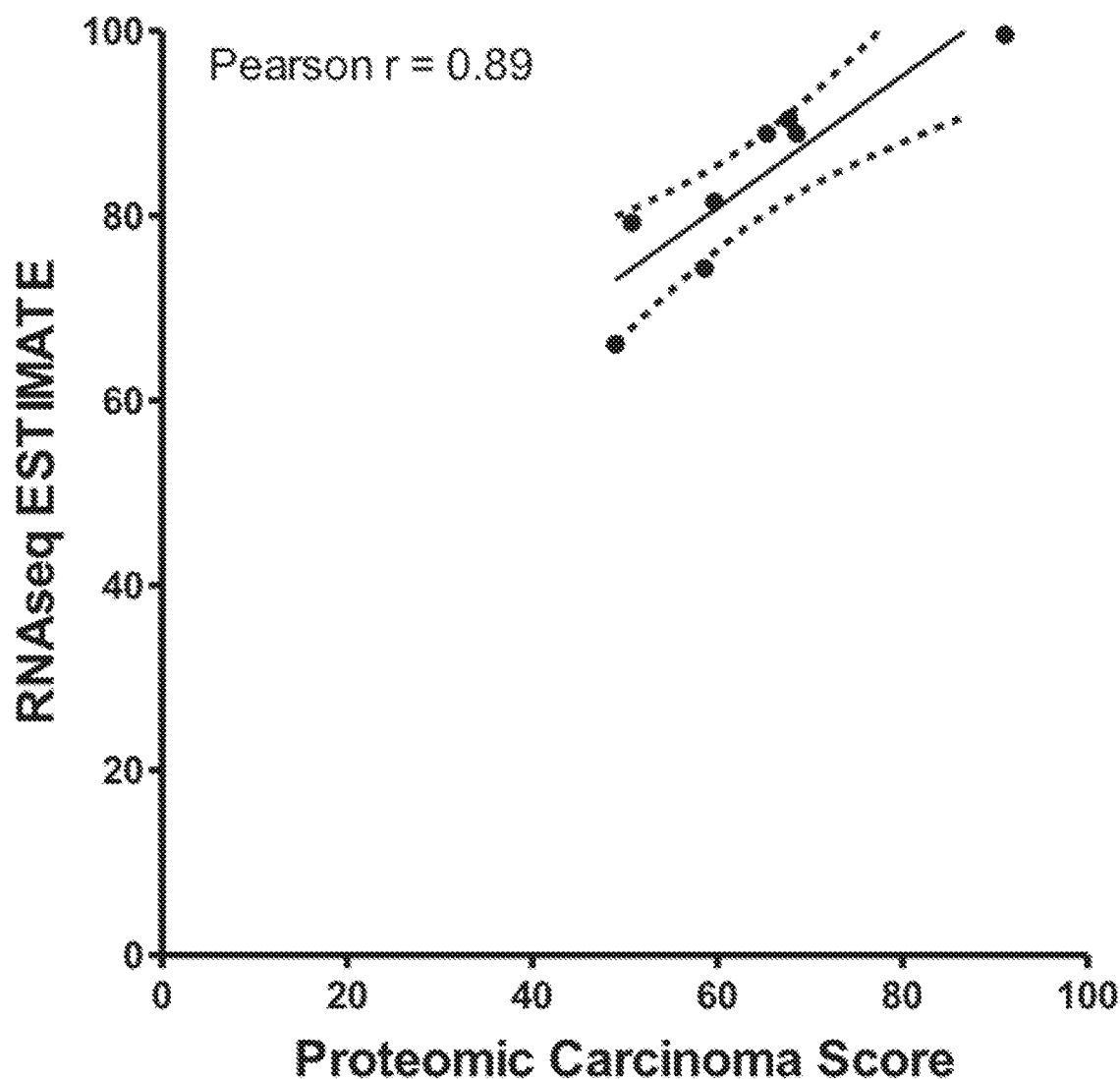
FIG. 5 illustrates the correlation between mRNA-derived ESTIMATE score and colon carcinoma component-specific protein signature (Proteomic Carcinoma score) in the estimation of carcinoma cell content of colon tumors.
Figure 6:
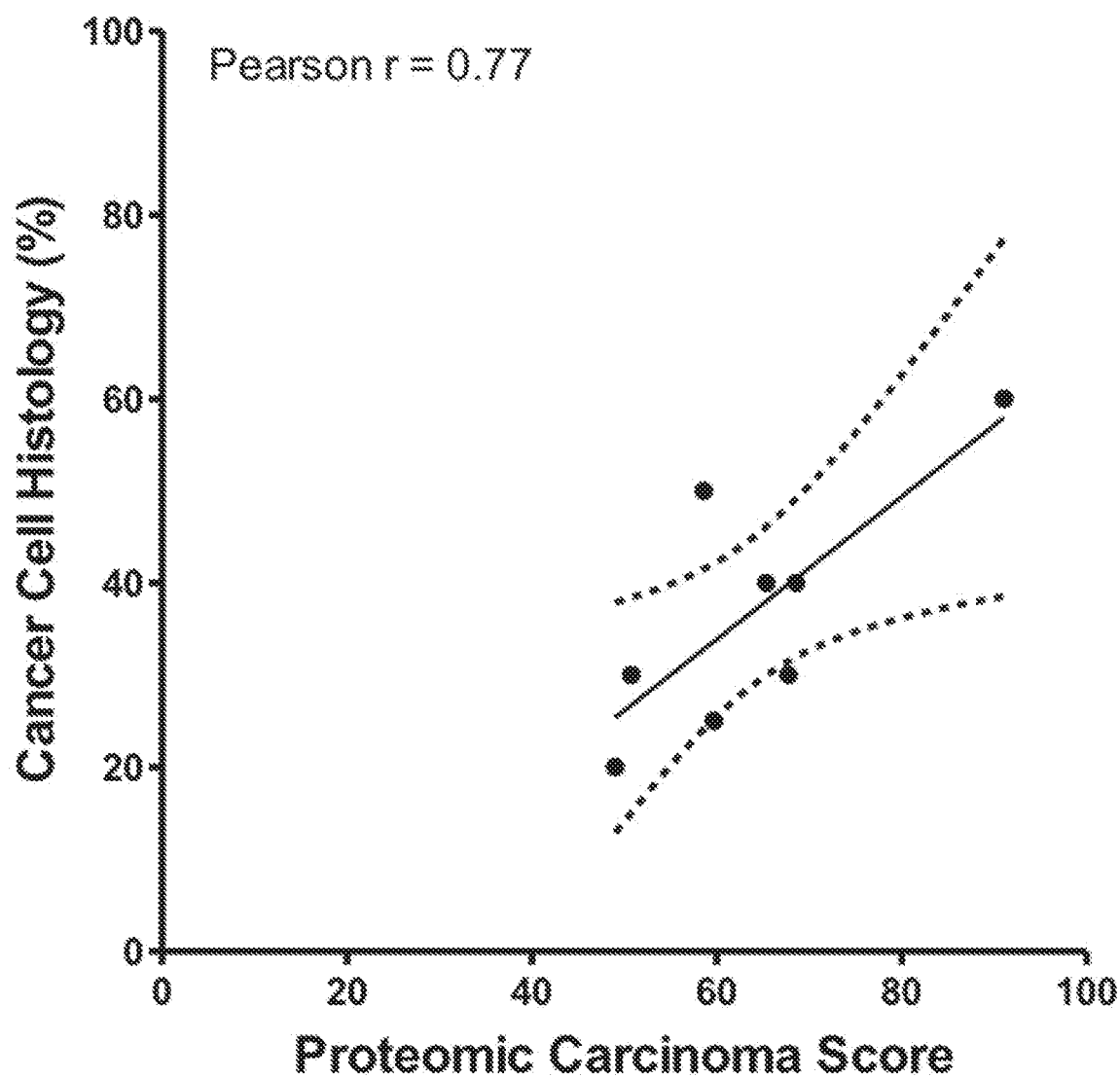
FIG. 6 illustrates the correlation between histological examination and colon carcinoma component-specific protein signature (Proteomic Carcinoma score) in the estimation of carcinoma cell content of colon tumors.

In a pure colon carcinoma cell preparation, the total proteomic signal from the 46 signature proteins is approximately 3% of the overall mass spectrometry signal. A robust quantification of this proportion is generated from pure carcinoma cells and used as a benchmark for carcinoma cell-proportion in a tumor sample of unknown purity. For instance, if the proteomic signal obtained from the carcinoma cell signature is 2.7% of the overall proteomic signal, then the purity of the tumor sample is estimated at 90% (2.7/3.0). This parameter is termed a Proteomic Carcinoma score. This protein-derived parameter was compared to an established method based on RNA sequencing (Yoshihara et al., *Inferring tumor cell purity and stromal and immune cell admixture from expression data*, Nat. Commun. 4:2612 (2013)), which generates an ESTIMATE score. The Proteomic Carcinoma score and the ESTIMATE score are highly correlated (Pearson correlation>0.89), as shown in FIG. 5. The Proteomic Carcinoma score also correlates with carcinoma cell percentage determined by histological examination of the samples (Pearson correlation>0.77) (FIG. 6). Although the Proteomic Carcinoma score is not used to correct measurement of the abundance of target proteins, this example demonstrates that measurement of a component-specific protein accurately represents the proportion of a biospecimen consisting of carcinoma cells.

For this example, the benchmark protein chosen was ACTB, which was measured through its proteotypic peptide GYSFTTTAER (SEQ ID NO: 1). The colon carcinoma component-specific protein chosen was RALY, which was measured through its proteotypic peptide GYAFVQYSNER (SEQ ID NO: 2). The proteotypic peptide selected for measurement of ERBB1 was IPLENLQIIR (SEQ ID NO: 3).

Calibration curves for all of the proteotypic peptides to be measured were generated using the following sample preparation workflow and mass spectrometry analysis platform, which was used for analysis of subsequent specimens. Synthetic (unlabeled ("light") and stable isotope labeled ("heavy")) standards for the benchmark proteotypic peptide GYSFTTTAER (ACTB) (SEQ ID NO: 1), the colon carcinoma component-specific proteotypic peptide GYAFVQYSNER (RALY) (SEQ ID NO: 2) and the ERBB1 proteotypic peptide IPLENLQIIR (SEQ ID NO: 3) were obtained from New England Peptide and were of >99% isotopic purity and >95% peptide purity as determined by HPLC-UV and LC-MS analysis. The heavy standards contained a C-terminal lysine or arginine uniformly labelled with $C^{13}$ and $N^{15}$. Absolute concentration of the heavy labelled peptides was determined by amino acid analysis. Eight-point calibration curves were generated for each peptide pair by spiking in a constant level of 5 fmol/μL of heavy peptide and varying the amount of light peptide from a high value of 100 fmol/μL to a low value of 0.025 fmol/μL. Assay linearity across all concentration points was assessed and an equation for determining the analyte concentration using the peak area ratio of light/heavy isotopomers was defined consistent with QuaSAR (Mani, D. R. et al., Statistical characterization of multiple-reaction monitoring mass spectrometry (MRM-MS) assays for quantitative proteomics. BMC Bioinformatics 13 Suppl 16, S9 (2012)) which was implemented through the Skyline interface as described (Addona, T. et al., Multi-site assessment of the precision and reproducibility of multiple reaction monitoring-based measurements of proteins in plasma, Nat Biotechnol 27:633-641 (2009)). For all SID assays, the heavy peptide was spiked in at 5 fmol/μL to enable normalization and absolute quantitation.

Tissue specimens were provided as 5 micron sections of formalin-fixed, paraffin-embedded tissue. Material from two sections was scraped using a razor blade and placed in 1.5 mL micro-centrifuge tubes. The paraffin was removed with three washes of 1 mL of the xylene substitute Sub-X and the tissue was rehydrated with two 1 mL washes each of 100%, 85%, and 70% ethanol. Deparaffinized, rehydrated tissue was re-suspended 100 μL of trifluoroethanol and 100 μL of 100 mM ammonium bicarbonate, pH 8. If additional buffer was required, equal volumes of trifluoroethanol and 100 mM ammonium bicarbonate pH 8.0, were added accordingly. Samples were sonicated using a Fisher Scientific Sonic Dismembrator Model 100 at a setting of 20 watts for 20 s followed by 30 s cooling on ice. This sonication step was repeated twice and samples were placed on ice between sonications. The resulting homogenate was heated with shaking at 1000 rpm for 1 h at 60° C. followed by a second series of sonication steps, as described above. A protein measurement was obtained for each sample using the BCA Protein Assay (ThermoFisher Pierce, Rockford, Ill.) using the manufacturer's protocol.

An aliquot equivalent to 100 μg protein was removed and reduced with dithiothreitol (50 mM) at 60° C. for 30 min followed by alkylation with iodoacetamide (100 mM) in the dark at room temperature for 20 min. The lysate was diluted with the appropriate volume of 50 mM ammonium bicarbonate, pH 8.0, to reduce the trifluoroethanol concentration to 10%, trypsin was added at a ratio of 1:50 (w/w) and digestion proceeded overnight at 37° C. The digested mixture was frozen at −80° C. and lyophilized to dryness. The lyophilized samples were re-suspended in 350 μL of high performance liquid chromatography (HPLC)-grade water and vortex mixed vigorously for one minute and desalted using an Oasis HLB 96-well μElution plate (30 μm particle size, 5 mg stationary phase content per well; Waters Corp., Milford, Mass.), in which each well was pre-washed with 500 μL of acetonitrile and equilibrated with 750 μL of HPLC-grade water. The flow-through was discarded and the plates were washed with 500 μL of HPLC-grade water and the peptides eluted with 80% acetonitrile and the eluates were evaporated to dryness in vacuo. Samples were stored in the freezer until further analysis. Upon analysis, samples were reconstituted with 2% acetonitrile/0.1% formic acid to a concentration of 0.5 μg/μL.

The peptides from colorectal carcinoma specimens were then analyzed by quantitative mass spectrometry, and proteotypic peptides representing ERBB1, carcinoma component-specific protein RALY, and benchmark protein ACTB were quantified for each specimen. Targeted mass spectrometry assays were performed on ThermoFisher Scientific Q Exactive instrument equipped with a Proxeon nLC1000 LC (ThermoFisher Scientific) and a Nanoflex source (ThermoFisher Scientific). The instrument analysis method used was parallel reaction monitoring (PRM), as described (Gallien, S., et al., *Targeted proteomic quantification on a quadrupole-Orbitrap mass spectrometer*, Mol. Cell. Proteomics 11:1709-1723 (2012)). For PRM analyses, peptides were separated on a 11 cm long column with a 0.075 μm internal diameter (New Objective, PF360-75-10-N-5) packed with 0.003 μm particle size and 120 Å pore size ReproSil-Pur C18-AQ resin (Dr. Maisch GmbH, Ammerbuch-Entringen, Germany) over a 100 min gradient: from 2-5% acetonitrile over 5 min then 5 to 35% acetonitrile over 85 min, then 35-90% acetonitrile over 3 min followed by 7 min at 90% acetonitrile, all at a flow rate of 300 nL/min. The PRM method consisted of an MS1 scan at 17,500 resolution with an AGC value of 3 e6, max injection time of 64 msec, and scan range from m/z 380-1500 recorded as a profile data. This was followed by 14 targeted MS2 scans at a resolution of 17,500 and with an AGC value of 1 e5, a max injection time of 80 msec, a 2.0 m/z isolation window, a fixed first mass of 150 m/z, normalized collision energy of 27, and recorded as profile data. The targeted-MS2 methods were analyzed using unscheduled acquisitions. PRM runs were analyzed using Skyline (MacLean B. et al., *Skyline: an open source document editor for creating and analyzing targeted proteomics experiments*, Bioinformatics 26:966-968 (2010)) and four to five transitions per peptide were used for quantitative analyses.

Figure 8:
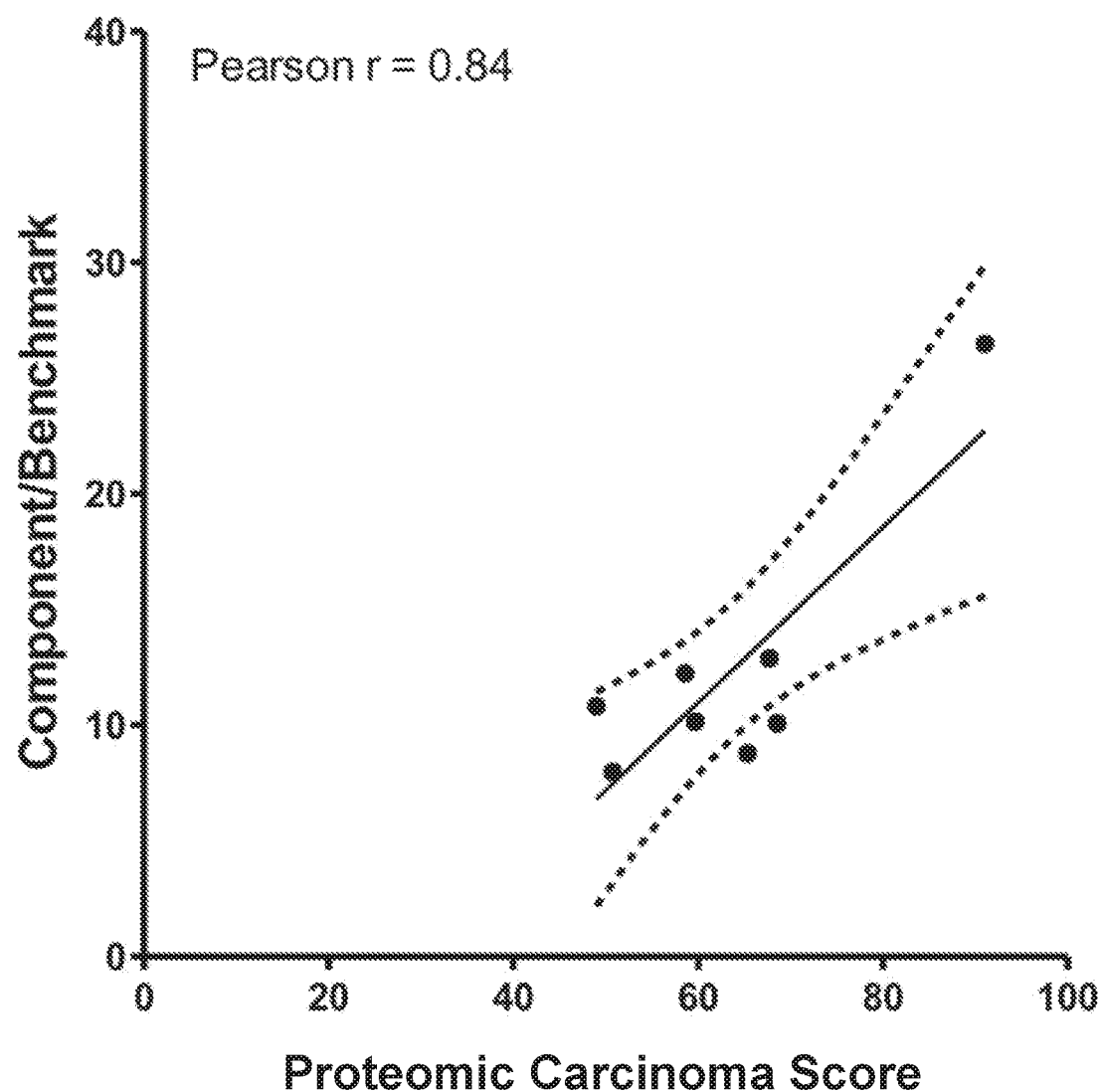
FIG. 8 illustrates the correlation between the calculated component-specific factors and colon carcinoma component-specific protein signature (Proteomic Carcinoma score) in the estimation of carcinoma cell content of colon tumors.

The measured amounts of ERBB1, the carcinoma component-specific protein RALY, and the benchmark protein ACTB in the specimens were then calculated from their quantified proteotypic peptides using their respective calibration curves (FIG. 7). The measured amount of the carcinoma component-specific protein RALY was divided by the measured amount of the benchmark protein ACTB to yield a carcinoma component-specific factor for each specimen, which is highly correlated with the Proteomic Carcinoma score, which was generated from data for 46 carcinoma signature proteins (FIG. 8).

ERBB1 measurements were divided by the carcinoma component-specific factor to generate a carcinoma cell component-adjusted ERBB1 content (ERBB1 target value) for each specimen (FIG. 7). Without adjustment, the measured values for ERBB1 vary from 0.2 to 2.5 fmol/microgram of protein. Through the application of the carcinoma component-specific adjustment, the measured values for ERBB1 are corrected for differing proportions of carcinoma cells and vary in proportion to carcinoma cell content. Comparison of ERBB1 protein abundance between different colorectal carcinoma specimens was made on the basis of the carcinoma cell component-adjusted ERBB1 content (ERBB1 target value) identified for each specimen. Comparison of ERBB1 target values between colon carcinoma specimens from different subjects, and/or comparison of ERBB1 target values from colon carcinoma specimens from different subjects with predetermined threshold values, may be used to identify subjects for treatment with ERBB1 antagonist drugs, such as administration of a therapeutically effective amount of cetuximab or administration of a therapeutically effective amount of panitumumab. Subjects may be treated with ERBB1 antagonist drugs, such as a therapeutically effective amount of cetuximab or a therapeutically effective amount of panitumumab if the ERBB1 target value for the subject exceeds a predetermined threshold target value.

Example 9

Measurement of ERBB2 in Breast Carcinoma Specimens by Mass Spectrometry of Proteolytic Peptides In another embodiment, the disclosed methods would be used to measure the abundance of the protein ERBB2 (Her2 protein), which is the target of the therapeutic drug traztuzumab in treatment of certain breast cancers. The configuration of an ERBB2 analysis for breast cancer specimens would proceed as set forth below.

Benchmark proteins are identified for breast cancer tumor specimens. Benchmark proteins in breast cancers may be identified from the dataset described by the National Cancer Institute Clinical Proteomic Analysis Tumor Consortium (available at https://cptac-data-portal.georgetown.edu/cptac-Public/) and may include proteins displaying less than 10% variation in abundance across the collection of 105 tumors described. Benchmark proteins identified in this way include ACTB, ACTG1, ACTG2, ANXA2, ENO3 and others.

Component-specific proteins are selected based on data obtained by mass spectrometry analysis of cell and stromal components collected from 150 breast tumors by laser capture microdissection. Breast cancer cell component-specific proteins identified in this way include NONO, RPL3, RPL4, LRPPRC, PDIA3, IDH2, HNRNPA3 and others. In addition, proteotypic peptides for the target protein ERBB2, benchmark proteins and breast cancer component-specific proteins are identified.

Calibration curves for all of the proteotypic peptides to be measured are generated using the mass spectrometry analysis platform to be used for analysis of subsequent specimens.

Proteins are extracted from breast cancer specimens and proteolytically cleaved to form peptides, peptides from breast carcinoma specimens are analyzed by quantitative mass spectrometry, and proteotypic peptides representing ERBB2, breast cancer component-specific proteins, and benchmark proteins are quantified for each specimen. The measured amounts of ERBB2, the breast cancer component-specific proteins, and benchmark proteins in the specimens are then calculated from their quantified proteotypic peptides using their respective calibration curves. The ratio of the measured amounts of the benchmark proteins to the measured amounts of breast cancer component-specific proteins is calculated to provide the breast cancer cell component factor for each specimen.

The measured amount of ERBB2 protein is multiplied by the breast cancer cell component factor, thereby generating a breast cancer cell component-adjusted ERBB2 content (ERBB2 target value). Comparison of ERBB2 protein abundance between different breast cancer specimens is made on the basis of the breast cancer cell component-adjusted ERBB2 content (ERBB2 target value) identified for each specimen. Comparison of ERBB2 target values between breast cancer specimens from different subjects, and/or comparison of ERBB2 target values from breast cancer specimens from different subjects with predetermined threshold values, may be used to select subjects for treatment with ERBB2 antagonist drugs, such as administration of a therapeutically effective amount of traztuzumab.

Example 10

Analysis of Immune Infiltration in Colon Carcinoma Specimens by Mass Spectrometry of Proteotypic Peptides In another embodiment, the disclosed methods will be used to measure T-cell infiltration of colorectal tumors, which is a determinant of the response of colorectal cancers to therapy with immune checkpoint inhibitor drugs, such as nivolumab.

Benchmark proteins are identified for colorectal carcinomas. Benchmark proteins in colorectal carcinomas can be identified from the dataset described by Zhang et al., *Proteogenomic characterization of human colon and rectal cancer*, Nature 513:382-387 (2014), and include proteins displaying less than 10% variation in abundance across the collection of 90 tumors described. Benchmark proteins identified in this way include ACTB, TUBA4A, IQGAP1, RPS3,AP1B1, EIF3K and WASF2.

Component-specific proteins are selected based on data obtained by mass spectrometry analysis of the carcinoma cell component collected from 18 colorectal tumors by laser capture microdissection. Carcinoma cell component-specific proteins identified in this way create a "carcinoma cell signature" of 46 proteins (BCAP31, CCT4, CCT6A, CYC1, DARS, DDX3X, DHX15, ECH1, EIF4A3, FASN, HNRNPA3, HNRNPAB, HNRNPL, HSD17B4, ILF3, IMMT, KARS, KHDRBS1, LGALS3BP, LRPPRC, PA2G4, PABPC1, PAICS, PRDX5, PSMA6, PSMA7, RAB14, RAB5C, RALY, RBMX, RHOA, RPL26, RPL28, RPL9, RPN2, RUVBL1, SF3B3, SHMT2, SLC12A2, SRSF1, SSB, TFRC, TMPO, TOP1, VDAC1, VDAC3).

In a pure colon carcinoma cell preparation, the total proteomic signal from the 46 signature proteins is approximately 3% of the overall mass spectrometry signal. A robust quantification of this proportion is generated from pure carcinoma cells and used as a benchmark for carcinoma cell-proportion in a tumor sample of unknown purity. For instance, if the proteomic signal obtained from the carcinoma cell signature is 2.7% of the overall proteomic signal, then the purity of the tumor sample is estimated at 90% (2.7/3.0). This parameter is termed a Proteomic Carcinoma score. This protein-derived parameter is compared to an established method based on RNA sequencing (Yoshihara et al., *Inferring tumor cell purity and stromal and immune cell admixture from expression data*, Nat. Commun. 4:2612 (2013)), which generates an ESTIMATE score. The Proteomic Carcinoma score and the ESTIMATE score are highly correlated (Pearson correlation >0.89), as shown in FIG. 5. The Proteomic Carcinoma score also correlates with carcinoma cell percentage determined by histological examination of the samples (Pearson correlation>0.77) (FIG. 6). Although the Proteomic Carcinoma score is not used to correct measurement of the abundance of target proteins, this example demonstrates that measurement of a component-specific protein accurately represents the proportion of a biospecimen consisting of carcinoma cells.

Target proteins selected as T cell marker proteins are identified as T cell receptor protein components CD3D, CD3E, CD3G, ZAP70, and TRAC and others. T cell marker proteins indicative of regulatory T cells (also known as Tregs) include the proteins CD4, FOXP3, and others. T cell marker proteins indicative of Cytotoxic T cells include the proteins CD8A, CD8B, and others. In addition, proteotypic peptides for the target proteins, benchmark proteins, and component-specific proteins are identified.

For this example, the benchmark protein chosen may be ACTB, which can be measured through its proteotypic peptide GYSFTTTAER (SEQ ID NO: 1). The colon carcinoma component-specific protein may be RALY, which can be measured through its proteotypic peptide GYAFVQYSNER (SEQ ID NO: 2). The target proteins may be CD4 and CD8B, which can be measured through their respective proteotypic peptides ILGNQGSFLTK (SEQ ID NO: 4) and GTIHGEEVEQEK (SEQ ID NO: 5).

Calibration curves for all of the proteotypic peptides to be measured are generated using the following sample preparation workflow and mass spectrometry analysis platform, which is used for analysis of subsequent specimens. Synthetic ("light") and stable isotope labeled ("heavy")) standards for the benchmark proteotypic peptide GYSFTTTAER (ACTB) (SEQ ID NO: 1), the colon carcinoma component-specific proteotypic peptide GYAFVQYSNER (RALY) (SEQ ID NO: 2), the CD4 target proteotypic peptide ILGNQGSFLTK (SEQ ID NO: 4) and the CD8B target proteotypic peptide GTIHGEEVEQEK (SEQ ID NO: 5) may be obtained from New England Peptide and should be of >99% isotopic purity and >95% peptide purity as determined by HPLC-UV and LC-MS analysis. The heavy standards contained a C-terminal lysine or arginine uniformly labelled with $C^{13}$ and $N^{15}$. Absolute concentration of the heavy labelled peptides can be determined by amino acid analysis. Eight-point calibration curves can be generated for each peptide pair by spiking in a constant level of 5 fmol/μL of heavy peptide and varying the amount of light peptide from a high value of 100 fmol/μL to a low value of 0.025 fmol/μL. Assay linearity across all concentration points can be assessed and an equation for determining the analyte concentration using the peak area ratio of light/heavy isotopomers can be defined consistent with QuaSAR (Mani, D. R. et al., Statistical characterization of multiple-reaction monitoring mass spectrometry (MRM-MS) assays for quantitative proteomics. BMC Bioinformatics 13 Suppl 16, S9 (2012)) which can be implemented through the Skyline interface as described (Addona, T. et al., Multi-site assessment of the precision and reproducibility of multiple reaction monitoring-based measurements of proteins in plasma, Nat Biotechnol 27:633-641 (2009)). For all SID assays, the heavy peptide can be spiked in at 5 fmol/μL to enable normalization and absolute quantitation.

Tissue specimens may be provided as 5 micron sections of formalin-fixed, paraffin-embedded tissue. Material from sections is scraped using a razor blade and placed in 1.5 mL micro-centrifuge tubes. The paraffin is removed with three washes of 1 mL of the xylene substitute Sub-X and the tissue is rehydrated with two 1 mL washes each of 100%, 85%, and 70% ethanol. Deparaffinized, rehydrated tissue can be re-suspended 100 μL of trifluoroethanol and 100 μL of 100 mM ammonium bicarbonate, pH 8. If additional buffer is required, equal volumes of trifluoroethanol and 100 mM ammonium bicarbonate pH 8.0, can be added accordingly. Samples are sonicated using a Fisher Scientific Sonic Dismembrator Model 100 at a setting of 20 watts for 20 s followed by 30 s cooling on ice. This sonication step is repeated twice and samples are placed on ice between sonications. The resulting homogenate is heated with shaking at 1000 rpm for 1 h at 60° C. followed by a second series of sonication steps, as described above. A protein measurement is obtained for each sample using the BCA Protein Assay (ThermoFisher Pierce, Rockford, Ill.) using the manufacturer's protocol.

An aliquot equivalent to 100 μg protein is removed and reduced with dithiothreitol (50 mM) at 60° C. for 30 min followed by alkylation with iodoacetamide (100 mM) in the dark at room temperature for 20 min. The lysate is diluted with the appropriate volume of 50 mM ammonium bicarbonate, pH 8.0, to reduce the TFE concentration to 10%, trypsin is added at a ratio of 1:50 (w/w) and digestion proceeded overnight at 37° C. The digested mixture is frozen at −80° C. and lyophilized to dryness. The lyophilized samples are re-suspended in 350 μL of high performance liquid chromatography (HPLC)-grade water and vortex mixed vigorously for one minute and desalted using an Oasis HLB 96-well μElution plate (30 μm particle size, 5 mg stationary phase content per well; Waters Corp., Milford, Mass.), in which each well is pre-washed with 500 μL of acetonitrile and equilibrated with 750 μL of HPLC-grade water. The flow-through is discarded and the plates are washed with 500 μL of HPLC-grade water, the peptides are eluted with 80% acetonitrile, and the eluates are evaporated to dryness in vacuo. Samples are stored in the freezer until further analysis. Upon analysis, samples are reconstituted with 2% acetonitrile/0.1% formic acid to a concentration of 0.5 μg/μL.

The peptides from colorectal carcinoma specimens are then analyzed by quantitative mass spectrometry, and proteotypic peptides representing CD4 and CD8B, carcinoma component-specific protein RALY, and benchmark protein ACTB are quantified for each specimen. Targeted mass spectrometry assays are performed on ThermoFisher Scientific Q Exactive instrument equipped with a Proxeon nLC1000 LC (ThermoFisher Scientific) and a Nanoflex source (ThermoFisher Scientific). The instrument analysis method can be parallel reaction monitoring (PRM), as described (Gallien, S., et al., *Targeted proteomic quantification on a quadrupole-Orbitrap mass spectrometer*, Mol. Cell. Proteomics 11:1709-1723 (2012)). For PRM analyses, peptides are separated on a 11 cm long column with a 0.075 μm internal diameter (New Objective, PF360-75-10-N-5) packed with 0.003 μm particle size and 120 Å pore size ReproSil-Pur C18-AQ resin (Dr. Maisch GmbH, Ammerbuch-Entringen, Germany) over a 100 min gradient: from 2-5% acetonitrile over 5 min then 5 to 35% acetonitrile over 85 min, then 35-90% acetonitrile over 3 min followed by 7 min at 90% acetonitrile, all at a flow rate of 300 nL/min. The PRM method consists of an MS1 scan at 17,500 resolution with an AGC value of 3 e6, max injection time of 64 msec, and scan range from m/z 380-1500 recorded as a profile data. This is followed by 14 targeted MS2 scans at a resolution of 17,500 and with an AGC value of 1 e5, a max injection time of 80 msec, a 2.0 m/z isolation window, a fixed first mass of 150 m/z, normalized collision energy of 27, and recorded as profile data. The targeted-MS2 methods are analyzed using unscheduled acquisitions. PRM runs are analyzed using Skyline (MacLean B. et al., *Skyline: an open source document editor for creating and analyzing targeted proteomics experiments*, Bioinformatics 26:966-968 (2010)) and four to five transitions per peptide can be used for quantitative analyses.

The measured amounts of target T-cell marker proteins, the carcinoma component-specific proteins, and benchmark proteins in the specimens will be calculated from their quantified proteotypic peptides using their respective calibration curves. The ratio of the measured amounts of the benchmark proteins to the measured amounts of carcinoma component-specific proteins is calculated to provide the carcinoma component factor for each specimen.

The measured amount of each target T-cell marker protein is multiplied by the carcinoma component factor, thereby generating a carcinoma cell component-corrected T-cell marker content (T-cell marker target value). A global T-cell/carcinoma enrichment value is calculated from target values for one or more of CD3D, CD3E, CD3G, ZAP70, TRAC, and others. A Treg/carcinoma enrichment value is calculated from target values for one or more of CD4, FOXP3, and others. A cytotoxic T-cell/carcinoma enrichment value is calculated from target values for one or more of CD8A, CD8B, and others. Comparison of T-cell infiltration between different colorectal carcinoma specimens is made on the basis of the global T cell/tumor enrichment values, the Treg/tumor enrichment values and the cytotoxic T cell/tumor enrichment values identified for each specimen. These values inform the choice of immunotherapeutics for treatment of cancers, such as melanoma, where a high degree of infiltration by cytotoxic T-cells is associated with a greater probability of therapeutic response to the immune checkpoint inhibitor pembrolizumab (Tumeh et al., *PD-1 blockade induces responses by inhibiting adaptive immune resistance*, Nature 515:568-571 (2014)). Carcinoma specimens with high cytotoxic T cell/tumor enrichment values and low Treg/tumor enrichment values also may be selected for therapy with other immune checkpoint inhibitors, such as nivolumab.

Example 11

Measurement of PD-L1 in Lung Adenocarcinoma Specimens by Immunoassay

In another embodiment, the disclosed methods would be used to measure the abundance of the protein PD-L1, which is the target of the therapeutic drug atezolizumab in treatment of lung adenocarcinomas. The configuration of a PD-L1 analysis for lung adenocarcinoma specimens would proceed as set forth below.

Benchmark proteins may be identified for adenocarcinoma specimens. Benchmark proteins in adenocarcinomas may be identified from the dataset described previously (Kikuchi et al., In-depth proteomic analysis of non-small cell lung cancer to discover molecular targets and biomarkers, Mol. Cell. Proteomics 11:916-932 (2012)) and may include proteins displaying less than 10% variation in abundance across the collection of adenocarcinomas and matched normal tissue described. Benchmark proteins identified in this way include SFN, HSP90B1, NPM1, THBS1, and others.

Lung adenocarcinoma component-specific proteins may be selected based on data obtained by mass spectrometry analysis of lung adenocarcinomas and normal lung tissue as described (Kikuchi et al., In-depth proteomic analysis of non-small cell lung cancer to discover molecular targets and biomarkers, Mol. Cell. Proteomics 11:916-932 (2012)) and may include proteins detected in adenocarcinomas and not detected in matched normal tissue. Lung adenocarcinoma component-specific proteins identified in this way include CALCA, CHGB, PCSK1, VIL1, and others.

The selection of antibody pairs for a sandwich ELISA is done through geometry testing experiments, in which the ability of candidate antibodies are first evaluated for the efficiency of capture of the target protein. Once the highest affinity capture reagent is identified, other antibodies are then evaluated for ability to label the capture complex. The detection antibody may be labeled with an enzyme, such as horseradish peroxidase to enable detection through action of the enzyme on a substrate to produce a product that can be detected by colorimetry. Alternatively, detection antibodies may be labeled with biotin, which enables coupling to streptavidin-conjugated enzymes that can produce colored or fluorescent products. Detection may be performed by colorimetric or fluorimetric detection in a 96-well or 384-well plate format. Other labeling options include conjugation of detection antibodies with electrochemiluminescent reagents, which enables luminescence detection when the assay is performed on an electrode-equipped analyzer. Other variations of the ELISA platform include femtoliter reaction vessel arrays or laser flow cytometry to enable detection of single molecule capture events, thereby offering sensitivity over 2-4 orders of magnitude greater than conventional plate-based ELISAs.

An alternative to plate-based and single-analyte ELISA is a multiplexed platform, in which a sandwich ELISA is performed on a bead-based system, where each bead contains a capture antibody directed against a different target protein and where each bead is also labeled with a distinct fluorophore. These bead-labeling fluorophores enable association of each bead in a mixture with the identity of the specific antibody immobilized on the bead. When a solution containing the target proteins is incubated with a mixture of the beads, the target proteins are captured by their cognate capture antibodies. Addition of a mixture of the detection antibodies labels each of the antibody-protein complexes, which are then detected by fluorescence in a flow stream that records the identity of each distinct bead-capture antibody complex and the fluorescence signal from the corresponding detection antibody. With this platform, multiplexed ELISAs are performed simultaneously.

Because the specificity of antibody-protein recognition may highly dependent on the folding and structure of the proteins to be analyzed, care must be taken to extract the proteins from the tissue under non-denaturing conditions. Thus extraction should be performed at neutral pH and with solutions of physiological ionic strength. Detergents may be used to enable protein solubilization during extraction, the detergents and chaotropic agents may denature proteins. Accordingly, each ELISA should be tested with protein standards under conditions to be used for tissue extraction to minimize artifactual effects on the measurements.

Calibration curves for a lung adenocarcinoma benchmark protein, a lung adenocarcinoma component-specific protein and PD-L1 are generated using the ELISA platform to be used for analysis of subsequent specimens.

Proteins are extracted from adenocarcinoma specimens and analyzed by ELISA, and PD-L1, lung adenocarcinoma component-specific proteins, and lung adenocarcinoma benchmark proteins are quantified for each specimen. The measured amounts of PD-L1, the lung adenocarcinoma component-specific protein, and benchmark protein in the specimens are then calculated from their ELISAs using their respective calibration curves. The ratio of the measured amount of the lung adenocarcinoma benchmark protein to the measured amount of lung adenocarcinoma component-specific protein is calculated to provide the lung adenocarcinoma cell component factor for each specimen.

The measured amount of PD-L1 protein is multiplied by the lung adenocarcinoma cell component factor, thereby generating a lung adenocarcinoma cancer cell component-adjusted PD-L1 content (PD-L1 target value). Comparison of PD-L1 protein abundance between different lung adenocarcinoma specimens is made on the basis of the lung adenocarcinoma cancer cell component-adjusted PD-L1 content (PD-L1 target value) identified for each specimen. Comparison of PD-L1 target values between lung adenocarcinoma specimens from different subjects, and/or comparison of PD-L1 target values from lung adenocarcinoma specimens from different subjects with predetermined threshold values, may be used to select subjects for treatment with PD-L1 antagonist drugs, such as administration of a therapeutically effective amount of atezolizumab.

Example 12

Measurement of PD-L1 in Lung Adenocarcinoma Specimens by Aptamer Assay

In another embodiment, the disclosed methods would be used to measure the abundance of the protein PD-L1, which is the target of the therapeutic drug atezolizumab in treatment of lung adenocarcinomas. The configuration of an PD-L1 analysis for lung adenocarcinoma specimens would proceed as set forth below.

Benchmark proteins may be identified for adenocarcinoma specimens. Benchmark proteins in adenocarcinomas may be identified from the dataset described previously (Kikuchi et al., *In-depth proteomic analysis of nonsmall cell lung cancer to discover molecular targets and biomarkers*, Mol. Cell. Proteomics 11:916-932 (2012)) and may include proteins displaying less than 10% variation in abundance across the collection of adenocarcinomas and matched normal tissue described. Benchmark proteins identified in this way include SFN, HSP90B1, NPM1, THBS1 and others.

Lung adenocarcinoma component-specific proteins may be selected based on data obtained by mass spectrometry analysis of lung adenocarcinomas and normal lung tissue as described (Kikuchi et al., *In-depth proteomic analysis of nonsmall cell lung cancer to discover molecular targets and biomarkers*, Mol. Cell. Proteomics 11:916-932 (2012)) and may include proteins detected in adenocarcinomas and not detected in matched normal tissue. Lung adenocarcinoma component-specific proteins identified in this way include CALCA, CHGB, PCSK1, VIL1 and others.

The generation of aptamer reagents directed against benchmark proteins, component-specific proteins, and the target protein PD-L1 is achieved by a process termed systematic evolution of ligands by exponential enrichment (SELEX), in which a diverse library of single stranded oligonucleotides of either RNA or DNA is contacted with the protein of interest. After removal of unbound sequences by wash steps, the bound oligonucleotides are released and this population (which contains sequences with higher affinity for the protein target) is amplified by polymerase chain reaction (for DNA sequences) or reverse transcriptase polymerase chain reaction followed by RNA transcription (for RNA sequences). The amplified oligonucleotide sequences are again contacted with the target protein and this selection cycle is repeated multiple times until a population of high affinity oligonucleotide sequences is obtained. Sequencing of the selected oligonucleotides identifies the highest affinity sequences, which then can be generated subsequently by synthesis. The optimized sequences can be refined further by targeted modification to obtain reagents of higher affinity and selectivity for the target protein. Further selectivity of aptamers can be achieved by incorporation of chemically modified nucleotides in the oligonucleotide sequences. The aptamers can be labeled with biotin, specialized primer sequences and a fluorophore to enable specific analysis steps in protein capture and detection.

Quantitative analysis of the benchmark proteins, component-specific proteins and the target protein PD-L1 with aptamers can be performed as described previously (Gold et al., *Aptamer-based multiplexed proteomic technology for biomarker discovery*, PloS One 5:e15004 (2010). A protein extract is prepared from the biospecimen to be analyzed and the proteins then are contacted with a mixture of the aptamers, which are labeled with biotin containing a UV photocleavable linker. The aptamer-protein complexes are then captured on streptavidin beads, which are washed to remove non-specifically bound proteins. The aptamer-protein complexes are released from the beads by UV photolysis of the cleavable linker, the proteins then are biotinylated and the aptamer-protein complexes are re-captured on monomeric avidin beads. After a wash step, the aptamer-protein complexes are released by treatment with excess biotin. The aptamer-protein complexes are then captured onto beads containing an oligonucleotide DNA primer sequence complementary to a tag sequence on all of the aptamers. The primer beads containing the captured aptamer-protein complexes are briefly treated with a basic pH solution to release non-specifically bound aptamer-protein complexes. Finally, the aptamers are released from the protein complexes and quantified by hybridization to a custom DNA microarray with fluorescence detection.

Because the specificity of aptamer-protein recognition may be highly dependent on the folding and structure of the proteins to be analyzed, care must be taken to extract the proteins from the tissue under non-denaturing conditions. Thus extraction should be performed at neutral pH and with solutions of physiological ionic strength. Detergents may be used to enable protein solubilization during extraction, the detergents and chaotropic agents may denature proteins. Accordingly, each aptamer assay should be tested with protein standards under conditions to be used for tissue extraction to minimize artifactual effects on the measurements.

Calibration curves for a lung adenocarcinoma benchmark protein, a lung adenocarcinoma component-specific protein and PD-L1 are generated using the aptamer analysis platform to be used for analysis of subsequent specimens.

Proteins are extracted from adenocarcinoma specimens and analyzed with the aptamer platform, and PD-L1, lung adenocarcinoma component-specific proteins, and lung adenocarcinoma benchmark proteins are quantified for each specimen. The measured amounts of PD-L1, the lung adenocarcinoma component-specific protein, and benchmark protein in the specimens are then calculated from their ELISAs using their respective calibration curves. The ratio of the measured amount of the lung adenocarcinoma benchmark protein to the measured amount of lung adenocarcinoma component-specific protein is calculated to provide the lung adenocarcinoma cell component factor for each specimen.

The measured amount of PD-L1 protein is multiplied by the lung adenocarcinoma cell component factor, thereby generating a lung adenocarcinoma cancer cell component-adjusted PD-L1 content (PD-L1 target value). Comparison of PD-L1 protein abundance between different lung adenocarcinoma specimens is made on the basis of the lung adenocarcinoma cancer cell component-adjusted PD-L1 content (PD-L1 target value) identified for each specimen. Comparison of PD-L1 target values between lung adenocarcinoma specimens from different subjects, and/or comparison of PD-L1 target values from lung adenocarcinoma specimens from different subjects with predetermined threshold values, may be used to select subjects for treatment with PD-L1 antagonist drugs, such as administration of a therapeutically effective amount of atezolizumab.

4. EXEMPLARY EMBODIMENTS

For reasons of completeness, various aspects of the disclosure are set out in the following numbered clauses:

Clause 1. A method for measuring the amount of a target protein in a heterogeneous biospecimen having two or more cell types, comprising: extracting proteins from a heterogeneous biospecimen; cleaving the proteins to form peptides; analyzing the peptides by mass spectrometry to measure an amount of a proteotypic peptide of a benchmark protein, an amount of a proteotypic peptide of a component-specific protein, and an amount of a proteotypic peptide of a target protein; quantifying an amount of the benchmark protein, an amount of the component-specific protein, and an amount of the target protein in the biospecimen based on the amounts of the corresponding proteotypic peptides; normalizing the amount of the component-specific protein to the amount of the benchmark protein to identify a component factor of a component cell type that expresses the component-specific protein; normalizing the amount of the target protein to the component factor of the component cell type to identify a component factor adjusted amount representing a target value of the target protein in the heterogeneous biospecimen.

Clause 2. A method for quantifying a target protein in a heterogeneous biospecimen, the method comprising: obtaining proteins extracted from a heterogeneous biospecimen; quantifying an amount of a benchmark protein, an amount of a component-specific protein, and an amount of a target protein extracted from the biospecimen; normalizing the amount of the component-specific protein to the amount of the benchmark protein to identify a component factor of a component cell type that expresses the component-specific protein; and normalizing the amount of the target protein to the component factor of the component cell type to identify a component factor adjusted amount of the target protein representing a target value of the target protein in the heterogeneous biospecimen.

Clause 3. The method of clause 2, wherein the proteins extracted from the heterogeneous biospecimen have been cleaved to form peptides and wherein the quantifying step is performed by mass spectrometry.

Clause 4. The method of clause 2, wherein the quantifying step is performed by immunoassay.

Clause 5. The method of clause 2, wherein the quantifying step is performed by aptamer affinity reagent assay.

Clause 6. The method of any of clauses 1-5, wherein the heterogeneous biospecimen comprises a neoplasm.

Clause 7. The method of clause 6, wherein the neoplasm comprises a cancer.

Clause 8. The method of clause 7, wherein the cancer is a carcinoma.

Clause 9. The method of clause 7, wherein the component cell type is a cancer.

Clause 10. The method of any of clauses 1-5, wherein the heterogeneous biospecimen comprises a biopsy.

Clause 11. The method of clause 10, wherein the biopsy is a needle biopsy.

Clause 12. The method of any of clauses 1-5, wherein the heterogeneous biospecimen comprises a biofluid specimen.

Clause 13. The method of clause 12, wherein the biofluid specimen comprises a blood specimen.

Clause 14. The method of any of clauses 1-5, wherein the heterogeneous biospecimen comprises exfoliated cells from buccal mucosa, urinary tract epithelium, airway epithelium, or gastrointestinal tract epithelium.

Clause 15. The method of any of clauses 1-5, wherein the heterogeneous biospecimen comprises human tumor xenograft tissue grown in a non-human host species.

Clause 16. The method of clause 15, wherein the component-specific protein is a human protein.

Clause 17. The method of clause 15, wherein the component-specific protein is a non-human host species protein.

Clause 18. The method of clause 15, wherein the target protein is a human protein.

Clause 19. The method of clause 16, wherein the target protein is a human protein.

Clause 20. The method of clause 1, wherein the cleaving step comprises contacting the proteins with a proteolytic enzyme.

Clause 21. The method of any of clauses 1-9, wherein the target protein is a sequence variant resulting from a single-nucleotide DNA polymorphism, a chromosomal rearrangement, or a somatic DNA mutation, insertion, deletion.

Clause 22. The method of any of clauses 1-5, wherein the target protein is a sequence variant arising during cellular RNA processing.

Clause 23. The method of any of clauses 1-9, wherein the component-specific protein is a protein characteristically expressed by cancer cell.

Clause 24. The method of clause 23, wherein the target protein is characteristically expressed by an immune cell.

Clause 25. The method of clause 24, wherein the component factor provides the cancer component factor of the heterogeneous biospecimen, and wherein the target value provides the immune cell enrichment value identifying the extent of infiltration by an immune cell into the heterogeneous biospecimen.

Clause 26. The method of any of clauses 1-9 or 23-25, wherein the heterogeneous biospecimen was obtained from a subject, further comprising administering an effective amount of a therapeutic drug to the subject if the target value of the target protein is above a threshold amount.

Clause 27. The method of any of clauses 1-9 or 23-25, wherein the heterogeneous biospecimen was obtained from a subject, further comprising administering an effective amount of a therapeutic drug to the subject if the target value of the target protein is below a threshold amount.

Clause 28. The method of any of clauses 1-9, wherein the target value of the target protein identifies the amount of the target protein in the component cell type.

Clause 29. The method of any of clauses 1-9, wherein the target protein is selected from proteomic analysis of cultured cells.

Clause 30. The method of clause 29, wherein the cultured cells comprise cultured cancer cells.

Clause 31. The method of any of clauses 1-9, wherein the target protein is selected by mass-spectrometry-based proteomic analysis of a cell type isolated from a heterogeneous biospecimen by dissection.

Clause 32. The method of clause 31, wherein the dissection comprises macrodissection or laser capture microdissection.

Clause 33. The method of any of clauses 1-9, wherein the component-specific protein is selected by mass-spectrometry-based proteomic analysis of a cell type isolated from a heterogeneous biospecimen by laser capture microdissection.

Clause 34. The method of any of clauses 1-9, wherein the benchmark protein is selected by mass-spectrometry-based proteomic analysis of a cell type isolated from a heterogeneous biospecimen by laser capture microdissection.

Clause 35. The method of any of clauses 1-5, wherein the target protein is selected by proteomic analysis of an intact neoplasm.

Clause 36. The method of any of clauses 1-5, wherein the target protein is selected by mRNA expression analysis of a neoplasm or cells cultured from a neoplasm.

Clause 37. The method of any of clauses 1-5, wherein the component-specific protein is selected by mRNA expression analysis of a neoplasm or cells cultured from a neoplasm.

Clause 38. The method of any of clauses 1-5, wherein the benchmark protein is selected by mRNA expression analysis of a neoplasm or cells cultured from a neoplasm.

Clause 39. The method of any of clauses 1-9, wherein the component factor is identified as the ratio of the measured amount of the benchmark protein to the measured amount of the component-specific protein.

Clause 40. The method of any of clauses 1-9, wherein the target value of the target protein in the heterogeneous biospecimen is indicative of a subtype of a cancer.

Clause 41. The method of any of clauses 1-9, further comprising selecting a treatment to treat a cancer in a subject based on the target value of the target protein in the heterogeneous biospecimen.

Clause 42. The method of clause 25, wherein the immune cell is one or more of a T-cell, a B-cell, and a macrophage.

Clause 43. The method of clause 25, wherein the heterogeneous biospecimen is a tumor specimen, and further comprising selecting a treatment for a subject to alter immune infiltration into the tumor based on immune cell enrichment value.

Clause 44. The method of clause 25, wherein the heterogeneous biospecimen is a tumor specimen, and further comprising selecting a treatment for a subject to activate an immune response against the tumor based on the immune cell enrichment value.

Clause 45. The method of clause 25, wherein the heterogeneous biospecimen is a tumor specimen; wherein the component factor identifies the extent of infiltration by an immune cell in the tumor; wherein the immune cell is one or more of a B-cell, a T-cell, and a macrophage; and further comprising selecting a treatment for a subject to activate an immune response against the tumor based on the immune cell enrichment value.

Clause 46. The method of any of clauses 1-9, wherein the biospecimen was obtained from a subject and further comprising providing a treatment to the subject based on the target value of the target protein in the biospecimen.

---

What is claimed is:

1. A method for preparing a target protein expressed in a cell type of interest in a heterogeneous biospecimen having two or more cell types, the method comprising:
   (a) extracting proteins from the heterogeneous biospecimen;
   (b) cleaving the proteins extracted in (a) with proteolytic enzymes or chemical reagents to produce peptides;
   (c) processing the peptides cleaved in (b);
   (d) measuring an amount (mass or a concentration) of a proteotypic peptide of a benchmark protein, a component-specific protein, and the target protein using mass spectrometry, wherein the amount of the benchmark protein, the component-specific protein, and the target protein in the biospecimen is quantified using a calibration curve based on stable isotope dilution;
   (e) determining a target value for the target protein by multiplying the amount of the target protein quantified in (d) by the ratio of the amount of the benchmark protein quantified in (d) to the amount of the component-specific protein quantified in (d); and;
   wherein when the target value exceeds a predetermined threshold concentration, an effective amount of a therapeutic drug that targets the target protein is administered to a subject.

2. The method of claim 1, wherein the heterogeneous biospecimen comprises a neoplasm, a biopsy, a biofluid specimen, or exfoliated cells from buccal mucosa, urinary tract epithelium, airway epithelium, or gastrointestinal tract epithelium.

3. The method of claim 2, wherein the neoplasm comprises a cancer, the biopsy comprises a needle biopsy, or the biofluid specimen comprises a blood specimen.

4. The method of claim 1, wherein the heterogeneous biospecimen comprises human tumor xenograft tissue grown in a non-human host species.

5. The method of claim 4, wherein the component-specific protein is a human protein or a non-human host species protein.

6. The method of claim 4, wherein the target protein is a human protein.

7. The method of claim 1, wherein the cleaving step comprises contacting the proteins with a proteolytic enzyme.

8. The method of claim 1, wherein the target protein is a sequence variant resulting from a single-nucleotide deoxyribonucleic add (DNA) polymorphism, a chromosomal rearrangement, or a somatic DNA mutation, insertion, deletion;
   a sequence variant arising during cellular ribonucleic add (RNA) processing;
   selected from proteomic analysis of cultured cells;
   selected by mass-spectrometry-based proteomic analysis of a cell type isolated from a heterogeneous biospecimen by dissection;
   selected by proteomic analysis of an intact neoplasm; or
   selected by messenger ribonucleic acid (mRNA) expression analysis of a neoplasm or cells cultured from a neoplasm.

9. The method of claim 1, wherein the component-specific protein is a protein expressed by a cancer cell.

10. The method of claim 9, wherein the target protein is expressed by an immune cell.

11. The method of claim 10, wherein the ratio of the component-specific protein expressed by a cancer cell to the benchmark protein defines a component factor;
   wherein the component factor represents a cancer cell fraction of the heterogeneous biospecimen; and
   wherein the target value provides an immune cell enrichment value that identifies the extent of infiltration by an immune cell into the heterogeneous biospecimen.

12. The method of claim 1, wherein the heterogeneous biospecimen was obtained from a subject, further comprising administering an effective amount of a therapeutic drug to the subject if the target value of the target protein is below a threshold amount.

13. The method of claim 1, wherein the target value of the target protein identifies the amount of the target protein in a component cell type or the target value of the target protein in the heterogeneous biospecimen is indicative of a subtype of a cancer.

14. The method of claim 1, wherein the component-specific protein is selected by mass-spectrometry-based proteomic analysis of a cell type isolated from a heterogeneous biospecimen by laser capture microdissection or selected by mRNA expression analysis of a neoplasm or cells cultured from a neoplasm.

15. The method of claim 1, wherein the benchmark protein is selected by mass-spectrometry-based proteomic analysis of a cell type isolated from a heterogeneous biospecimen by laser capture microdissection or selected by mRNA expression analysis of a neoplasm or cells cultured from a neoplasm.

16. The method of claim 1, wherein a proportional content of any cell in a tissue is identified as the ratio of the measured amount of the component-specific protein to the measured amount of the benchmark protein.

17. The method of claim 1, further comprising selecting a treatment to treat a cancer in a subject based on the target value of the target protein in the heterogeneous biospecimen.

18. The method of claim 11, wherein the heterogeneous biospecimen comprises a tumor specimen, and further comprising selecting a treatment for a subject to alter immune infiltration into a tumor based on the immune cell enrichment value or selecting a treatment for a subject to activate an immune response against the tumor based on the immune cell enrichment value.

19. The method of claim 11, wherein the heterogeneous biospecimen comprises a tumor specimen; wherein the component factor identifies the extent of infiltration by an immune cell in a tumor; wherein the immune cell is one or more of a B-cell, a T-cell, and a macrophage; and further comprising selecting a treatment for a subject to activate an immune response against the tumor based on the immune cell enrichment value.

20. The method of claim 1, wherein the biospecimen was obtained from a subject and further comprising providing a treatment to the subject based on the target value of the target protein in the biospecimen.

21. The method of claim 1, wherein step (c) comprises lyophilizing the peptides cleaved in (b) and resuspending the lyophilized peptides in a solvent.

* * * * *

SEQUENCE LISTING

```
<160> NUMBER OF SEQ ID NOS: 5

<210> SEQ ID NO 1
<211> LENGTH: 10
<212> TYPE: PRT
<213> ORGANISM: Artificial sequence
<220> FEATURE:
<223> OTHER INFORMATION: Proteotypic peptide

<400> SEQUENCE: 1

Gly Tyr Ser Phe Thr Thr Thr Ala Glu Arg
1               5                   10

<210> SEQ ID NO 2
<211> LENGTH: 11
<212> TYPE: PRT
<213> ORGANISM: Artificial sequence
<220> FEATURE:
<223> OTHER INFORMATION: Proteotypic peptide

<400> SEQUENCE: 2

Gly Tyr Ala Phe Val Gln Tyr Ser Asn Glu Arg
1               5                   10

<210> SEQ ID NO 3
<211> LENGTH: 10
<212> TYPE: PRT
<213> ORGANISM: Artificial sequence
<220> FEATURE:
<223> OTHER INFORMATION: Proteotypic peptide

<400> SEQUENCE: 3

Ile Pro Leu Glu Asn Leu Gln Ile Ile Arg
1               5                   10
```

```
<210> SEQ ID NO 4
<211> LENGTH: 11
<212> TYPE: PRT
<213> ORGANISM: Artificial sequence
<220> FEATURE:
<223> OTHER INFORMATION: Proteotypic peptide

<400> SEQUENCE: 4

Ile Leu Gly Asn Gln Gly Ser Phe Leu Thr Lys
1               5                   10

<210> SEQ ID NO 5
<211> LENGTH: 12
<212> TYPE: PRT
<213> ORGANISM: Artificial sequence
<220> FEATURE:
<223> OTHER INFORMATION: Proteotypic peptide

<400> SEQUENCE: 5

Gly Thr Ile His Gly Glu Glu Val Glu Gln Glu Lys
1               5                   10
```